United States Patent [19]

Van Wauwe et al.

[11] Patent Number: 5,157,046
[45] Date of Patent: Oct. 20, 1992

[54] METHOD OF TREATING EPITHELIAL DISORDERS

[75] Inventors: Jean P. F. Van Wauwe; Alfons H. M. Raeymaekers, both of Beerse, Belgium

[73] Assignee: Janssen Pharmaceutica N.V., Beerse, Belgium

[21] Appl. No.: 434,962

[22] Filed: Nov. 13, 1989

Related U.S. Application Data

[63] Continuation-in-part of Ser. No. 277,152, Nov. 29, 1988, abandoned.

[51] Int. Cl.$^5$ ............... C07D 211/68; C07D 211/80; C07D 413/04; A61K 31/41; A61K 31/495; A61K 31/44

[52] U.S. Cl. .................................. 514/397; 514/269; 514/314; 514/316; 514/318; 514/322; 514/333; 514/338; 514/359; 514/383; 514/383; 514/844; 514/859; 514/863; 544/333; 546/167; 546/187; 546/193; 546/194; 546/199; 546/256; 546/271; 548/181; 548/165; 548/255; 548/259; 548/260; 548/261; 548/266.4; 548/305.1; 548/306.1

[58] Field of Search ............... 514/859, 863, 844, 383, 514/384, 359, 333, 338, 269, 314, 316, 318, 322, 397; 546/167, 187, 193, 194, 199, 256, 271; 544/333; 548/181, 165, 336, 255, 259, 260, 261, 266.4

[56] References Cited

U.S. PATENT DOCUMENTS 4,859,684  8/1989  Raeymaekers ...................... 548/327

FOREIGN PATENT DOCUMENTS 0293978  12/1988  European Pat. Off. .

OTHER PUBLICATIONS

Mahler et al., THERAPEUTIC PROGRESS IN UROLOGICAL CANCERS, 303, 1989, Proceedings of an International Symposium, Paris, 29 Jun.–1 Jul. 1988, editors G. P. Murphy et al., pp. 205–210, Alan R. Liss, Inc., New York, US —"The effects of a new imidazole derivative in advanced prostatic cancer. A preliminary report".

Primary Examiner—Johann Richter
Attorney, Agent, or Firm—Charles J. Metz

[57] ABSTRACT

A method for treating skin disorders in warm-blooded animals, said method comprising administering to said warm-blooded animals an effective amount of an appropriately substituted benzimidazole or benzotriazole which suppresses the metabolism of retinoids. Compositions comprising said compounds and an effective amount of a retinoid.

18 Claims, No Drawings

METHOD OF TREATING EPITHELIAL DISORDERS

CROSS-REFERENCE TO RELATED APPLICATIONS

This application is a continuation-in-part of copending application Ser. No. 277,152, filed on Nov. 29, 1988, now abandoned.

BACKGROUND OF THE INVENTION

Retinoids, in particular retinoic acid and its derivatives, are substances which are known to have a broad spectrum of biological activity. More specifically, these substances affect the differentiation, maintenance and proliferation of various cell types. The ability of retinoids, such as, all-trans-retinoic acid, 13-cis-retinoic acid, and their derivatives to modulate differentiation in several cell types, whether they are of epithelial or mesenchymal origin, is extensively studied and reviewed in J. Clin. Chem. Clin. Biochem., 26, 479–488 (1983); Pharmacological Reviews, 36, 935-1005 (1984) and Arch. Dermatol., 117, 160-180 (1981).

It is known that certain retinoids, particularly the retinoic acids, are used topically for treatment of acne as set forth in U.S. Pat. No. 3,729,568. Other known uses of retinoic acid were reviewed in the Journal of American Academy of Dermatology, 4, 505-516 (1981) and the Journal of Medical Chemistry, 25, 1269-1277 (1982) and include, in addition to acne treatment, treatment of senile comedones, nevus comedonicus, linear verrucous nevus, plantar warts, pseudofolliculitis, keratoacanthoma, solar keratosis of extremities, callosities, keratosis palmaris et plantaris, Darier's disease, ichthyosis, psoriasis, acanthosis nigricans, lichen planus, molluscum contagiosum, reactive perforating collagenosis, melasma, corneal epithelial abrasion, Fox-Fordyce disease, cutaneous metastatic melanoma and keloids or hypertrophic scars.

Retinoids such as, all-trans-retinoic acid, 13-cis-retinoic acid and their derivatives, have also been used in the treatment of carcinomas.

There are however a number of drawbacks associated with the therapeutic applications of retinoids. The topical applications of retinoids on the one hand often cause significant irritation and peeling due to the relatively high concentrations of retinoid which have to be applied. Systemic applications on the other hand are limited by the toxicity and rapid degradation of the administered retinoids.

The compounds of the invention overcome the problems associated with art known retinoid therapy by suppressing the metabolism of endogenous or exogenously administered retinoic acid.

DESCRIPTION OF THE INVENTION

The present invention provides a method of treating mammals suffering from disorders which are characterized by an increased proliferation and/or abnormal differentiation of epithelial cells, by the systemic or topical administration to said mammals of an effective amount of an appropriately substituted benzimidazole or benzotriazole which suppresses the plasma elimination of endogenous or exogenously administered retinoic acid. A number of appropriately substituted benzimidazoles or benzotriazoles are disclosed in our applications U.S. Pat. No. 4,859,684 and U.S. Ser. No. 223,486 which corresponds to EP-A 293,978. Particular compounds for use in the present invention are compounds of formula (I)

and/or (II)

a pharmaceutically acceptable acid addition salt thereof or a stereochemically isomeric form thereof, wherein
R, $R^1$, $R^2$, $-A^1=A^2-A^3=A^4-$ and A in formula (I) have the following meaning
$-A^1=A^2-A^3=A^4-$ is a bivalent radical having the formula $$-CH=N-CH=CH- \quad (x);$$

$$-CH=N-CH=N- \quad (y); \text{ or}$$

$$-CH=N-N=CH- \quad (z);$$

R is hydrogen or $C_{1-6}$alkyl;
$R^1$ is hydrogen; $C_{1-10}$alkyl; $C_{3-7}$cycloalkyl; $Ar^1$ or $Ar^1-C_{1-6}$alkyl;
$R^2$ is hydrogen; $C_{3-7}$cycloalkyl; $Ar^1$; $C_{1-10}$alkyl; $C_{1-6}$alkyl substituted with $Ar^1$ or $C_{3-7}$cycloalkyl; hydroxy; $C_{1-10}$alkyloxy; $C_{1-6}$alkyloxy substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$-oxy;
A is a bivalent radical having the formula $$-CR^3=N- \text{ (a) or } -\overset{\overset{\displaystyle X}{\|}}{C}-NR^4- \text{ (b)}.$$

wherein the carbon atom in the bivalent radical (a) and (b) is connected to $-NR^2$;
said $R^3$ being hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, $C_{3-7}$cycloalkyl, quinolinyl, indolinyl or hydroxy; $C_{1-10}$alkyloxy; $C_{1-6}$alkyloxy substituted with $Ar^1$ or $C_{3-7}$cycloalkyl; $C_{2-6}$alkenyl optionally substituted with $Ar^1$; $Ar^2$-oxy; $C_{1-6}$alkyloxycarbonyl; carboxyl; $C_{1-6}$alkylcarbonyl; $Ar^1$-carbonyl or $Ar^1-(CHOH)-$;
said X being O or S;
said $R^4$ being hydrogen, $C_{1-6}$alkyl or $Ar^2-C_{1-6}$alkyl;
wherein $Ar^1$ is phenyl, substituted phenyl, pyridinyl, aminopyridinyl, imidazolyl, thienyl, halothienyl, furanyl, halofuranyl or thiazolyl; and $Ar^2$ is phenyl or substituted phenyl; said substituted phenyl in $Ar^1$ and $Ar^2$ being phenyl substituted with 1, 2 or 3 substituents each independently selected from halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl; and wherein R, $R^5$, $R^6$, $R^7$ and $—A^1=A^2—A^3=A^4—$ in formula (II) have the following meaning $—A^1=A^2—A^3=A^4—$ is a bivalent radical having the formula

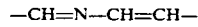  (x);

  (y); or

  (z);

R is hydrogen or $C_{1-6}$alkyl;

$R^5$ is hydrogen; $C_{1-10}$alkyl; $C_{3-7}$cycloalkyl; $Ar^3$; $Ar^4—C_{1-6}$alkyl; $C_{2-6}$alkenyl or $C_{2-6}$alkynyl;

$R^6$ is hydrogen; $C_{1-10}$alkyl optionally substituted with $Ar^3$, $C_{3-7}$cycloalkyl, hydroxy or $C_{1-6}$alkyloxy; $Ar^3$; $C_{2-6}$alkenyl; $C_{2-6}$alkynyl; $C_{3-7}$cycloalkyl; bicyclo[2.2.1]heptan-2-yl; 2,3-dihydro-1H-indenyl; 1,2,3,4-tetrahydronaphthalenyl; or a radical of formula $OR^7$, $R^7$ is hydrogen; $C_{2-6}$alkenyl optionally substituted with $Ar^4$; $C_{2-6}$alkynyl; pyrimidinyl; di($Ar^4$)methyl; 1-$C_{1-4}$alkyl-4-piperidinyl; or $C_{1-10}$alkyl optionally substituted with halo, hydroxy, $C_{1-6}$alkyloxy, amino, mono- and di($C_{1-6}$alkyl)-amino, trifluoromethyl, carboxyl, $C_{1-6}$alkyloxycarbonyl, $Ar^3$, $Ar^4—O—$, $Ar^4—S—$, $C_{3-7}$cycloalkyl, 2,3-dihydro-1,4-benzodioxinyl, 1H-benzimidazolyl, $C_{1-4}$alkyl substituted 1H-benzimidazolyl, (1,1'-biphenyl)-4-yl or with 2,3-dihydro-2-oxo-1H-benzimidazolyl;

$R^8$ is hydrogen, nitro, amino, mono- and di($C_{1-6}$alkyl)amino, halo, $C_{1-6}$alkyl, hydroxy or $C_{1-6}$alkyloxy;

wherein $Ar^3$ is phenyl, substituted phenyl, naphthalenyl, pyridinyl, aminopyridinyl, imidazolyl, triazolyl, thienyl, halothienyl, furanyl, $C_{1-6}$alkylfuranyl, halofuranyl or thiazolyl; $Ar^4$ is phenyl, substituted phenyl or pyridinyl, said substituted phenyl in $Ar^3$ and $Ar^4$ being phenyl substituted with up to 3 substituents each independently selected from halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro. Preferably said substituted phenyl is phenyl substituted with one or two substituents each independently selected from halo, $C_{1-6}$alkyl, $C_{1-6}$alkyloxy and trifluoromethyl.

As used in the foregoing definitions the term halo is generic to fluoro, chloro, bromo and iodo; the term "$C_{1-6}$alkyl" is meant to include straight chained and branched saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-10}$alkyl" is meant to include $C_{1-6}$alkyl radicals, as defined hereinabove, and the higher homologs thereof having from 7 to 10 carbon atoms; the term "$C_{3-7}$cycloalkyl" is generic to cyclopropyl, cyclobutyl, cyclopentyl, cyclohexyl and cycloheptyl. "$C_{2-6}$alkenyl" defines straight chained and branched hydrocarbon radicals containing one double bond having from 2 to 6 carbon atoms such as, for example, ethenyl, 2-propenyl, 3-butenyl, 2-butenyl, 2-pentenyl, 3-methyl-2-butenyl and the like; "$C_{2-6}$alkynyl" defines straight chained and branched hydrocarbon radicals containing one triple bond and having from 2 to 6 carbon atoms such as, for example, 2-propynyl, 2-butynyl, 3-butynyl, 2-pentynyl, 3-pentynyl, 4-pentynyl and the like; and when a $C_{2-6}$alkenyl or a $C_{2-6}$alkynyl is substituted on a heteroatom, then the carbon atom of said $C_{2-6}$alkenyl or said $C_{2-6}$alkynyl connected to said heteroatom preferably is saturated.

It is to be understood that the

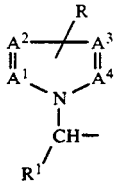

moiety in formula (I) and the

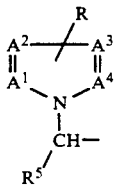

moiety in formula (II), both hereinafter refered as the 1H-azol-1-ylmethyl moiety, may be substituted on either the 4, 5, 6 or 7 position of the benzimidazole or benzotriazole heterocyclic ring, preferably on the 5 or 6 position, with the 5 position being preferred.

It is evident that the compounds of formula (I) may also contain in their structure a tautomeric system and consequently these compounds can be present in each of their tautomeric forms.

Particular compounds for use in the method of the present invention are those compounds of formula (I) wherein the 1H-azol-1-ylmethyl moiety is substituted on either the 5 or 6 position of the benzimidazole ring; and/or R is hydrogen; and/or $R^1$ is hydrogen; $C_{1-6}$alkyl; $C_{3-7}$cycloalkyl; phenyl; substituted phenyl; thienyl or furanyl optionally substituted with halo; and/or $R^2$ is hydrogen; $C_{3-7}$cycloalkyl; phenyl; substituted phenyl; pyridinyl; $C_{1-6}$alkyl optionally monosubstituted with phenyl, $C_{3-7}$cycloalkyl, pyridinyl or thienyl; hydroxyl, $C_{1-6}$alkyloxy optionally monosubstituted with phenyl, pyridinyl, thienyl or $C_{3-6}$cycloalkyl; $C_{3-6}$alkenyloxy optionally monosubstituted with phenyl; or $C_{3-6}$alkynyloxy; and/or $R^3$ is hydrogen; $C_{1-4}$alkyl substituted with up to 4 halo atoms; $C_{3-7}$cycloalkyl; phenyl; substituted phenyl; imidazolyl; thiazolyl; thienyl; furanyl; quinolinyl; pyridinyl optionally substituted with amino, $C_{1-10}$alkyl; $C_{1-5}$alkyl optionally monosubstituted with phenyl, pyridinyl, imidazolyl, thienyl, indolyl or hydroxyl; $C_{1-4}$alkyloxy optionally monosubstituted with phenyl; $C_{2-6}$alkenyl optionally monosubstituted with pyridinyl, furanyl, imidazolyl or phenyl; carboxyl; $C_{1-4}$alkyloxycarbonyl; phenylcarbonyl; or hydroxy and phenylmethyl; and/or $R^4$ is hydrogen or phenyl$C_{1-4}$alkyl.

Other particular compounds for use in the method of the present invention are those compounds of formula (II) wherein the 1H-azol-1-ylmethyl moiety is substituted on either the 5 or 6 position of the benzotriazole ring; and/or R is hydrogen; and/or $R^5$ is hydrogen; $C_{1-6}$alkyl; phenyl; substituted phenyl; $C_{3-7}$cycloalkyl; thienyl or furanyl optionally substituted with halo; and/or $R^6$ is hydrogen; $C_{1-6}$alkyl; $C_{3-6}$alkenyl; $C_{3-6}$alkynyl; $C_{3-7}$cycloalkyl; phenyl; substituted phenyl; substituted phenyl; bicylo[2.2.1]heptan-2-yl; 2,3-dihydro-1H-indenyl; 1,2,3,4-tetrahydronaphthalenyl; $C_{1-6}$alkyl monosubstituted with phenyl, substituted phenyl, naphthalenyl, thienyl, furanyl, $C_{1-4}$alkylfuranyl, $C_{3-7}$cycloalkyl, hydroxy, $C_{1-4}$alkyloxy; or $R^6$ is a radical $-OR^7$ with $R^7$ being hydrogen, $C_{1-6}$alkyl, $C_{3-6}$alkenyl, phenyl$C_{3-6}$alkenyl, $C_{3-6}$alkynyl, pyrimidinyl, diphenylmethyl, (1-$C_{1-4}$alkyl-4-piperidinyl), $C_{1-6}$alkyl substituted with halo, hydroxy, amino, mono- or di($C_{1-6}$alkyl)amino, trifluoromethyl, carboxyl, $C_{1-6}$alkyloxycarbonyl, phenyl, substituted phenyl, thienyl, furanyl, $C_{1-4}$alkylfuranyl, pyridinyl, phenoxy, phenylthio, 2,3-dihydro-1,4-benzodioxinyl, 1H-benzimidazolyl, $C_{1-4}$alkyl substituted 1Hbenzimidazolyl, (1,1'-biphenyl)-4-yl or 2,3-dihydro-2-oxo-1H-benzimidazolyl; and/or $R^8$ is hydrogen.

More particular compounds for use in the method of the present invention are those particular compounds of formula (I) wherein $R^1$ is hydrogen, $C_{1-6}$alkyl, phenyl, substituted phenyl, thienyl or furanyl; $R^2$ is hydrogen, $C_{1-6}$alkyl, or $C_{1-4}$alkyl substituted with phenyl; $R^3$ is hydrogen, $C_{1-6}$alkyl, phenyl, pyridinyl, $C_{1-6}$alkyl, $C_{1-6}$alkyl monosubstituted with phenyl or $C_{2-6}$alkenyl optionally monosubstituted with furanyl or phenyl; and $R^4$ is hydrogen.

Other more particular compounds of the present invention are those particular compounds of formula (II) wherein $R^5$ is hydrogen, $C_{1-6}$alkyl, phenyl, substituted phenyl, thienyl or furanyl; $R^6$ is hydrogen, $C_{1-6}$alkyl, $C_{1-6}$alkyl substituted with phenyl, or a radical of formula $-OR^7$ with $R^7$ being hydrogen or $C_{1-6}$alkyl.

Preferred compounds for use in the method of the present invention are those particular compounds of formula (I) wherein $R^1$ is $C_{1-4}$alkyl, phenyl, phenyl substituted with one or two halo, $C_{1-4}$alkyl or $C_{1-4}$alkyloxy substituents, or thienyl; $R^2$ is hydrogen or $C_{1-4}$alkyl; and $R^3$ is hydrogen or $C_{1-4}$alkyl.

Other preferred compounds for use in the method of the present invention are those particular compounds of formula (II) wherein $R^5$ is $C_{1-4}$alkyl, phenyl or phenyl substituted with one or two halo, $C_{1-4}$alkyl or $C_{1-4}$alkyloxy substituents; and $R^6$ is hydrogen or $C_{1-4}$alkyl.

More preferred compounds for use in the method of the present invention are those preferred compounds of formula (I) wherein $R^1$ is phenyl or halophenyl, and $R^2$ and $R^3$ are both independently hydrogen or $C_{1-4}$alkyl.

Other more preferred compound for use in the method of the present invention are those preferred compounds of formula (II) wherein $R^5$ is phenyl or halophenyl and $R^6$ is hydrogen or $C_{1-4}$alkyl.

Most preferred compounds for use in the method of the present invention are 5-[(1H-imidazol-1-yl)phenylmethyl]-1H-benzimidazole, (±)-5-[(1H-imidazol-1-yl)phenylmethyl]-2-methyl-1H-benzimidazole, 5-[(1H-imidazol-1-yl)phenylmethyl]-1-methyl-1H-benzimidazole, 5-[1-(1H-imidazole-1-yl)-2-methylpropyl]-2-methyl-1H-benzimidazole, 5-[(3-chlorophenyl)(1H-imidazol-1-yl)methyl]-1H-benzimidazole or (±)-5-[(1H-imidazol-1-yl)phenylmethyl]-2-methyl-1H-benzimidazole, the pharmaceutically acceptable acid addition salts and possible stereoisomers thereof.

The compounds of formula (I) and (II) can be prepared by N-alkylating an azole of formula (III) or an alkali metal salt thereof with a benzimidazole of formula (IV) or a benzotriazole of formula (V).

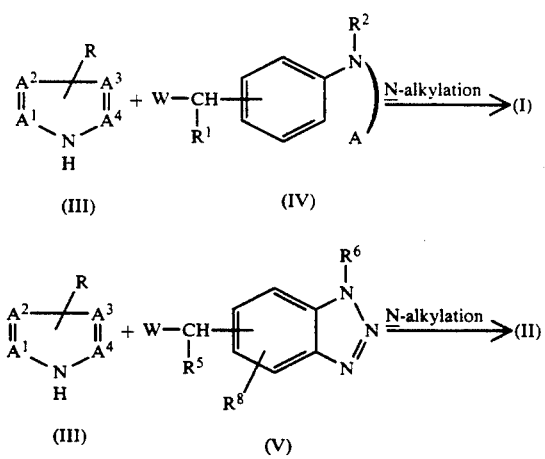

In formula (IV) and (V) W represents an appropriate reactive leaving group such as, for example, halo, e.g. fluoro, chloro, bromo, iodo or a sulfonyloxy group, e.g. 4-methylbenzenesulfonyloxy, benzenesulfonyloxy, 2-naphthalenesulfonyloxy, methanesulfonyloxy, trifluoromethanesulfonyloxy and the like reactive leaving groups.

The above described N-alkylations are conveniently carried out by stirring the reactants in the presence of a suitable solvent such as, for example, an aromatic hydrocarbon, e.g., benzene, methylbenzene, dimethylbenzene, and the like; an ester, e.g. ethyl acetate, γ-butyrolacetone and the like; a ketone, e.g. 2-propanone, 4-methyl-2-penta-none and the like; an ether, e.g., 1,4-dioxane, 1,1'-oxybisethane, tetrahydrofuran and the like; a polar aprotic solvent, e.g., N,N-dimethylformamide, N,N-dimethyl-acetamide, dimethyl sulfoxide, 1-methyl-2-pyrrolidinone, acetonitrile, hexamethylphosphor triamide, 1,3-dimethyl-3,4,5,6-tetrahydro-2(1H)-pyrimidinone, 1,3-dimethyl-2-imidazolidinone, benzonitrile and the like; and mixtures of such solvents. Somewhat elevated temperatures may be appropriate to enhance the rate of the reaction and in some cases the reaction may even be carried out at the reflux temperature of the reaction mixture. The addition of an appropriate base such as, for example, an alkali or an earth alkaline metal carbonate, hydrogen carbonate, hydroxide, amide or hydride, e.g., sodium hydroxide, potassium hydroxide, potassium carbonate, sodium hydride and the like or an organic base, such as, for example, N,N-dimethyl-4-pyridinamine, pyridine, N,N-diethylethanamine or N-(1-methylethyl)-2-propanamine may be employed to pick up the acid which is liberated during the course of the reaction. In some instances it may be advantageous to use an excess of the azole (III) or to convert the azole first into a suitable salt form thereof such as, for example, an alkali or earth alkaline metal salt, by reacting (III) with an appropriate base as defined hereinabove and subsequently using said salt form in the reaction with the alkylating reagents of formulae (IV) or (V). Additionally, it may be advantageous to conduct said N-alkylation reaction under an inert atmosphere such as, for example, oxygen-free argon or nitrogen gas. Said alkylation may also be carried out by applying art-known conditions of phase transfer catalysis reactions.

Compounds of formula (I) and (II) wherein $-X^1=X^2-$ is a bivalent radical of formula (x), said compounds being represented by formula (I-x) and (II-x), may also be prepared by reacting a benzimidazole (IV) or benzotriazole (V) with a 1-protected imidazole of formula (III-x) following the N-alkylation procedures described hereinabove for the preparation of compounds of formula (I) or (II) starting from (III) and (IV) and from (III) and (V).

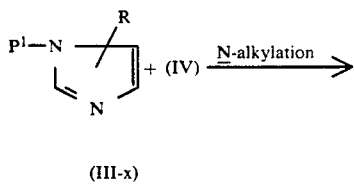

(III-x)

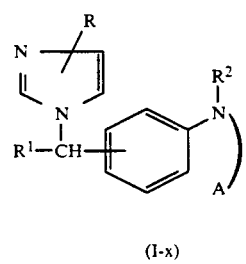

(I-x)

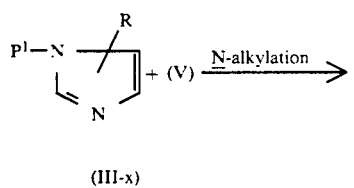

(III-x)

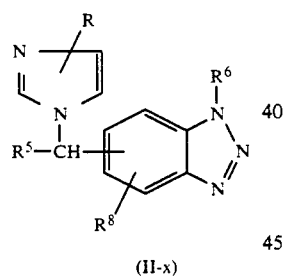

(II-x)

In (III-x) P¹ represents a protective group such as, for example, $C_{1-6}$alkylcarbonyl, $C_{1-6}$alkyloxycarbonyl, arylcarbonyl or a tri($C_{1-6}$alkyl)silyl group. In some instances the reaction of (III-x) with (IV) or (V) first yields a 1-protected imidazolium salt of formula (VI-a) or (VI-b) which may in situ, or if desired, after isolating and further purifying it, be deprotected by stirring it in an aqueous basic solution or acidic solution.

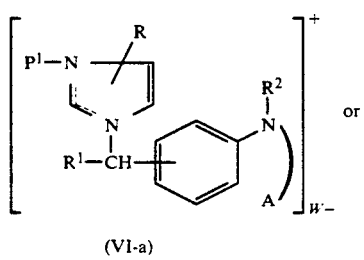

(VI-a)

-continued

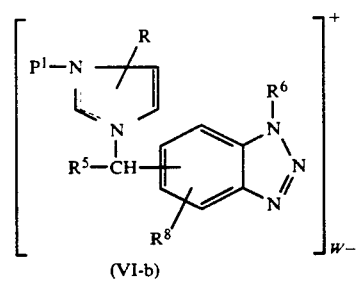

(VI-b)

In (VI-a) and (VI-b) $W^-$ is an anion arising from an acid such as, for example, hydrochloric acid, hydrobromic acid, methanesulfonic acid, 4-methylbenzenesulfonic acid and the like acids.

Compounds of formula (I) and (II) wherein $-X^1=X^2-$ is a bivalent radical of formula (y), said compounds being represented by formula (I-y) and (II-y), can also be prepared by endo-N-alkylation of a triazolamine of formula (III-y) with a benzimidazole (IV) and a benzotriazole (V) and subsequent deamination of the thus prepared triazolium salt, wherein $W^-$ is an anion as defined hereinabove.

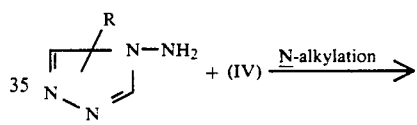

(III-y)

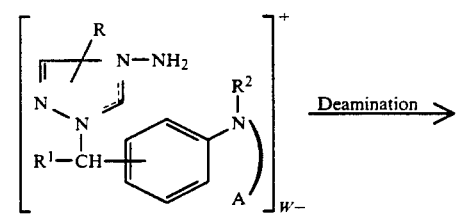

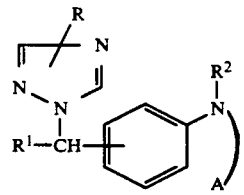

(I-y)

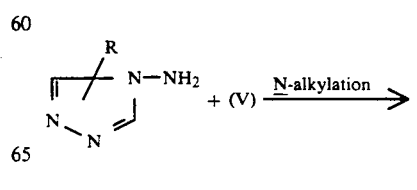

(III-y)

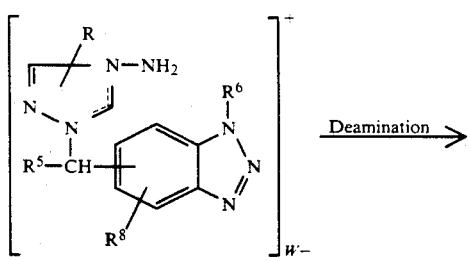

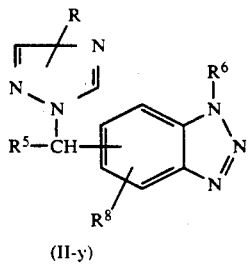

(II-y)

The endo-N-alkylation reaction of (III-y) with (IV) or (V) is carried out according to similar procedures as described hereinabove for the preparation of a compound of formula (I) starting from (III) and (II). Said deamination reaction is conveniently conducted by reaction with an acidic nitrite solution in the presence of an appropriate reductant, or by reaction with an alkylnitrite such as, for example, 1,1-dimethylethyl nitrite or isoamylnitrite and the like. Preferably, said deamination reaction is conducted with an aqueous solution of nitrous acid or of a nitrite salt in a suitable acid in the presence of a reducing agent such as, for example, hypophosphorous acid, formic acid, at a lower temperature.

The compounds of formulae (I) and (II) may also be prepared by reacting an intermediate of formula (VII) or (VIII) with a reagent of formula (IX) such as, for example, a 1,1'-carbonylbis[1H-imidazole].

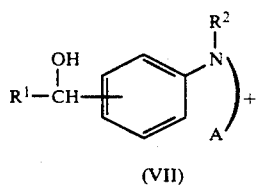

(VII)

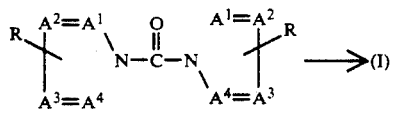

(IX)

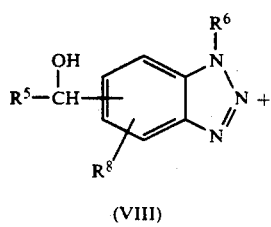

(VIII)

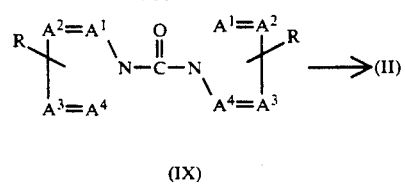

(IX)

Said reactions may conveniently be conducted in a suitable solvent such as, for example, an ether, e.g., 1,4-dioxane, tetrahydrofuran; a halogenated hydrocarbon, e.g., di- or trichloromethane; a hydrocarbon, e.g., benzene, methylbenzene; N,N-dimethylformamide, N,N-dimethylacetamide, or mixtures of such solvents. In order to enhance the reaction rate, it may be advantageous to heat the reaction mixture.

The compounds of formula (I) may also be prepared by reacting a ketone or aldehyde of formula (X) or (XI) with an azole (III) in the presence of formic acid or formamides as reducing agents.

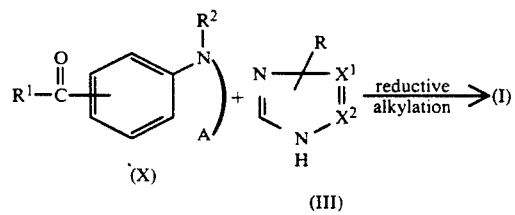

(X)   (III)

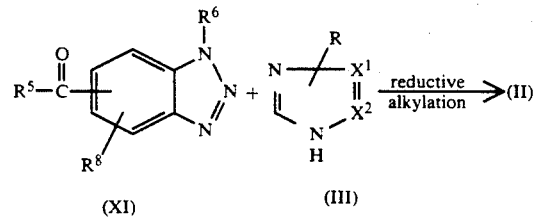

(XI)   (III)

The compounds of formula (I) and (II) can alternatively be prepared according to cyclization procedures outlined in the art for the preparation of benzimidazoles from benzenediamines or ortho nitrobenzeneamines, e.g. U.S. Pat. No. 4,859,684, or for the preparation of benzotriazoles starting from appropriate benzenediamines or halonitrobenzene derivatives, e.g. U.S. Ser. No. 223,486, which corresponds to EP-A-293,978.

For example, benzimidazoles of formula (I) can be prepared by cyclizing an appropriately substituted 1,2-benzenediamine with a carboxylic acid or a functional derivative thereof such as, for example the halide, anhydride, amide and ester form thereof in a suitable acidic medium. The above and similar cyclization procedures for making the compounds of formula (I) are outlined in U.S. Pat. No. 4,859,684 which is incorporated herein by reference.

The benzotriazoles of formula (II) wherein $R^6$ is other than $OR^7$, said compounds being represented by formula (II-a) and said radical by $R^{6-a}$, can generally be prepared from an appropriate aromatic diamine of formula (XII) by reaction with a suitable diazotizing reagent.

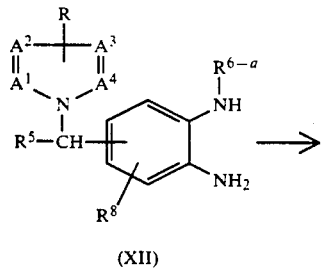

(XII)

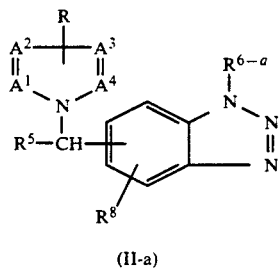

(II-a)

Suitable diazotizing reagents are alkylnitrites, e.g. 1,1-dimethylethylnitrite, isoamylnitrite and the like; nitronium tetrafluoroborate, nitrous acid in aqueous solution, or more particularly aqueous solutions of nitrite salts such as, for example, sodium nitrite, potassium nitrite, silver nitrite and the like, in the presence of a mineral and/or organic acid such as, for example, hydrohalic acids, e.g. hydrochloric, hydrobromic and the like acids; perchloric acid, perbromic acid, periodic acid, phosphoric acid, sulfuric acid, nitric acid and the like; carboxylic acids, e.g. formic, acetic, trifluoroacetic, propanoic, benzoic, methanesulfonic and the like acids.

Said reaction can conveniently be conducted by stirring the aromatic diamine of formula (XII) in the presence of a suitable diazotizing reagent as defined hereinabove, at a low temperature, in an aqueous solution, optionally in admixture with organic cosolvents such as, for example, alkanols, e.g. methanol, ethanol and the like.

The compounds of formula (II) wherein $R^7$ is other than hydrogen, said compounds being represented by formula (II-b) and said radical by $R^{7-a}$, can generally be prepared by O-alkylating a compound of formula (II) wherein $R^7$ is hydrogen, said compounds being represented by formula (II-c), with an appropriate alkylating reagent of formula $R^{7-a}$—W (XIII).

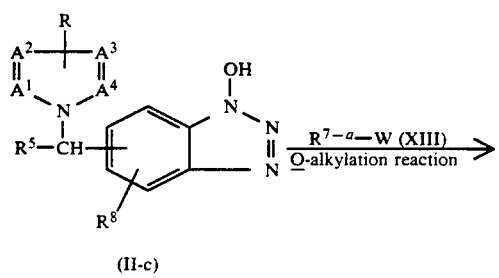

(II-c)

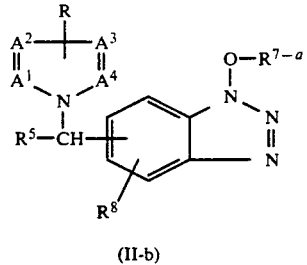

(II-b)

In formula (XIII) and hereinafter W represents an appropriate reactive leaving group such as, for example, halo, e.g. chloro, bromo, iodo, or a sulfonyloxy group, e.g. 4-methylbenzenesulfonyloxy, benzenesulfonyloxy, 2-naphthalenesulfonyloxy, methanesulfonyloxy, trifluoromethanesulfonyloxy and the like reactive leaving groups.

Said O-alkylation reaction can conveniently be carried out by mixing the reactants, optionally in a reaction-inert solvent such as, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 4-methyl-2-pentanone and the like; an ester, e.g. ethyl acetate, $\gamma$-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, an amine, e.g. N,N-diethylethanamine, N-(1-methylethyl)-2-propanamine, 4-ethylmorpholine, 1,4-diazabicyclo[2.2.2]octane, pyridine and the like, may optionally be used to pick up the acid which is formed during the course of the reaction. Further, it may be advantageous to convert the compound (II-c) first into a suitable salt form thereof such as, for example, an alkali or earth alkaline metal salt, by reacting (II-c) with an appropriate base as defined hereinabove and subsequently using said salt form in the reaction with the alkylating reagent of formula (XIII). In some instances the addition of an iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said O-alkylation under an inert atmosphere such as, for example, oxygen-free argon or nitrogen gas. Alternatively, said O-alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

The compounds of formula (II-c) in turn can be prepared by cyclizing an appropriately substituted nitrobenzene derivative of formula (XIV) wherein $W^1$ represents a reactive leaving group, with hydrazine, a hydrate thereof or an acid addition salt thereof.

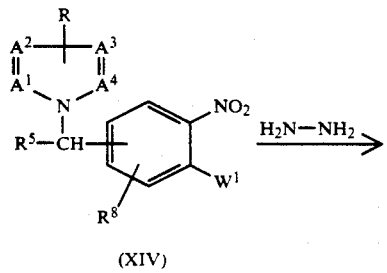

(XIV)

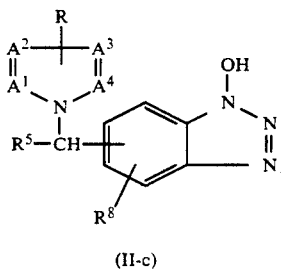

(II-c)

The reactive leaving group $W^1$ represents, groups such as, for example, halo, e.g. chloro, bromo or preferably fluoro, nitro, sulfonyloxy groups, e.g. methanesulfonyloxy, 4-methylbenzenesulfonyloxy and the like, aryloxy, $C_{1-6}$alkyloxy or $C_{1-6}$alkylthio and the like groups. Said cyclization may be carried out by stirring the reactants in a reaction-inert solvent such as, for example, an alkanol, e.g. methanol, ethanol, 2-propanol, 1-butanol and the like, an aromatic hydrocarbon, e.g. benzene, methylbenzene, dimethylbenzene and the like, or a mixture of such solvents. Somewhat elevated temperatures may be appropriate to enhance the rate of the reaction and preferably the reaction is carried out at the reflux temperature of the reaction mixture.

The compounds of formula (II-a) wherein $R^{7-a}$ is hydrogen, said compounds being represented by formula (II-a-1) may also be prepared from the compounds of formula (II-c) following art-known reduction procedures.

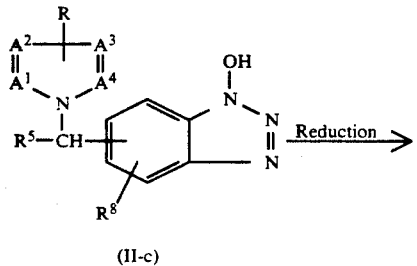

(II-c)

-continued

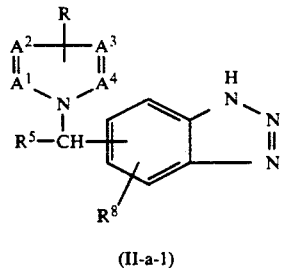

(II-a-1)

Said reduction may be conducted, for example, by catalytic hydrogenation in the presence of hydrogen and an appropriate hydrogenation catalyst such as, for example, platinum, palladium, platinum(IV) oxide, Raney-nickel and the like, in the presence of a reaction inert organic solvent such as, for example, an alkanol, e.g. methanol, ethanol, 2-propanol, butanol and the like.

Said reduction may alternatively be conducted by reducing the starting material with a reducing agent such as, for example, titanium(III)chloride or tin(II)chloride in hydrochloric acid, optionally in the presence of a reaction-inert solvent. Preferably said reduction is carried out by converting the hydroxy group into a readily leaving group, such as, for example, an ether —O—$CH_2$—Z wherein Z is an electronwithdrawing group such as cyano, $C_{1-6}$alkyloxycarbonyl, aminocarbonyl, mono- or di($C_{1-6}$alkyl)aminocarbonyl and the like, by reaction with an O-alkylating reagent of formula W—$CH_2$—Z, and stirring the thus obtained ether intermediates in the presence of a base such as, for example, an alkali or earth alkaline metal carbonate, hydrogen carbonate, hydroxide, alkoxide or amide, in an appropriate solvent such as, for example, a dipolar aprotic solvent, e.g. dimethyl sulfoxide, N,N-dimethylformamide and the like solvents, thus eliminating OHC—Z and yielding the desired benzotriazole of formula (II-a-1). Said O-alkylation and elimination can easily be conducted in a one-pot procedure.

The compounds of formula (II) wherein $R^6$ is other than hydrogen and $OR^7$, said compounds being represented by formula (II-a-2) and said radical by $R^{6-b}$, may be prepared by N-alkylating a compound of formula (II-a-1) with a reagent of formula $R^{6-b}$—W, wherein W is a leaving group as defined hereinabove.

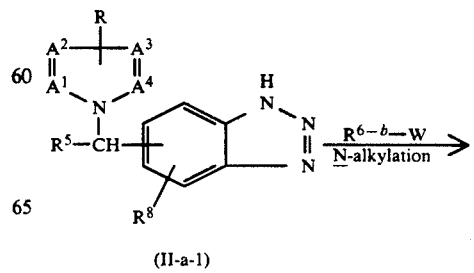

(II-a-1)

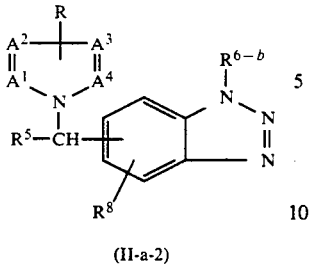

(II-a-2)

Said N-alkylation reaction of (I-a-1) may conveniently be conducted following the procedures described hereinabove for the preparation of the compounds of formula (II-b) from the compounds of formula (II-c).

Alternatively, some compounds of formula (I) and (II) may also be prepared according to procedures analogous to those described in the literature for the preparation of azoles by cyclizing an appropriate starting material.

The compounds of formula (I-x) and (II-x) may also be prepared, for example, by cyclizing an intermediate of formula (XV) or (XVI) and desulfurating the thus obtained intermediate of formula (XVII) or (XVIII).

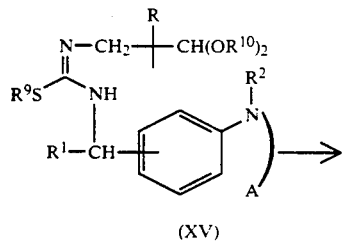

(XV)

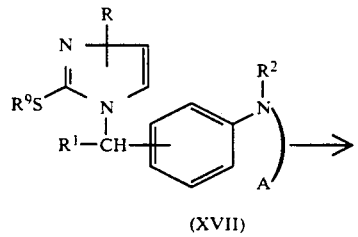

(XVII)

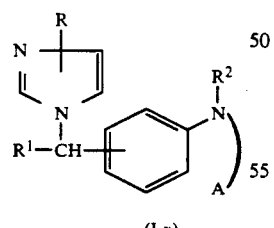

(I-x)

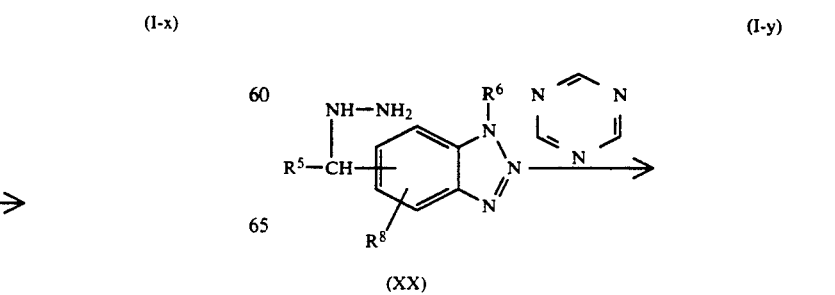

(XVI)

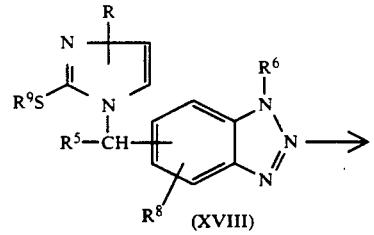

(XVIII)

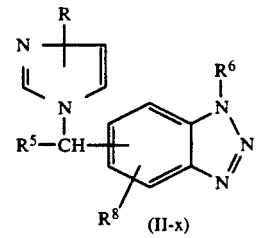

(II-x)

In formulae (XV) and (XVI) and (XVII) and (XVIII) $R^9$ represents hydrogen or $C_{1-6}$alkyl and $R^{14}$ represents $C_{1-6}$alkyl or both $R^{10}$ taken together form a $C_{2-3}$alkanediyl radical.

Said cyclization reaction may conveniently be conducted by stirring and heating an intermediate (XV) or (XVI) in an aqueous acidic solvent, e.g. in aqueous hydrochloric or sulfuric acid. The thus obtained intermediate (XVII) or (XVIII) may be desulfurated following art-known procedures, e.g., by treatment with Raney nickel in the presence of an alkanol, e.g. methanol, ethanol and the like, or by treatment with nitric acid, optionally in the presence of sodium nitrite.

The compounds of formula (I-y) and (II-y) may be prepared from a hydrazine derivative of formula (XIX) or (XX) by reaction with s-triazine following the procedures described in J. Org. Chem., 1956, 1037.

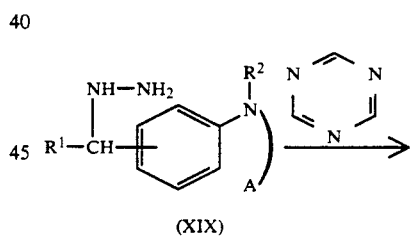

(XIX)

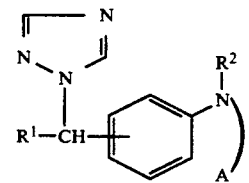

(I-y)

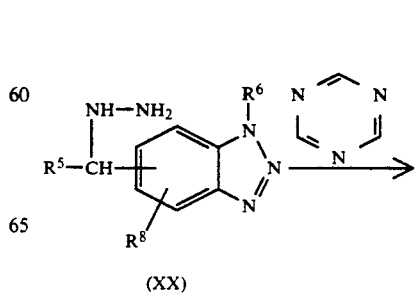

(XX)

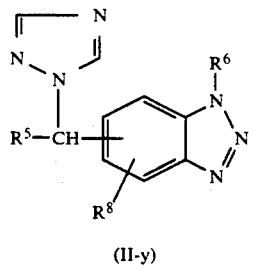

(II-y)

The intermediate hydrazine (XIX) or (XX) and the corresponding intermediate amines may also be converted into azoles, wherein —A$^1$=A$^2$—A$^3$=A$^4$— is a bivalent radical of formula (x), (y) or (z) following procedures described in U.S. Pat. No. 4,267,179, incorporated herein by reference.

The intermediates and the starting materials in the foregoing are known and may be prepared according to art-known methodologies of preparing said or similar compounds. Intermediates and starting compounds in the preparation are specifically described in U.S. Pat. No. 4,859,684 which is incorporated herein by reference. Intermediates of formula (II) are described in U.S. Ser. No. 223,486 which corresponds to EP-A-293,978. A number of such preparation methods will be described hereinafter in more detail.

The intermediates of formula (XII) can generally be prepared from the corresponding nitro derivatives of formula (XXI) by reaction with an appropriate reducing agent.

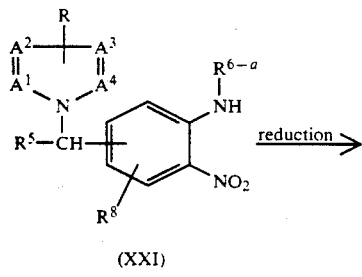

(XXI)

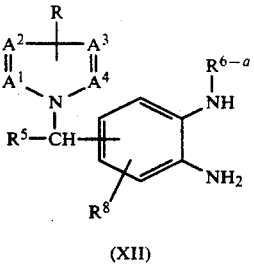

(XII)

Suitable reducing agents for use in the above nitro-to-amine reduction are, for example, hydrogen in the presence of an appropriate hydrogenation catalyst such as, for example, palladium-on-charcoal, platinum-on-charcoal, Raney-nickel and the like catalysts. Said reduction can conveniently be conducted in a reaction inert solvent such as, for example, an alkanol, e.g. methanol, ethanol, 2-propanol and the like, optionally at an elevated pressure and/or temperature. Alternatively said reduction can also be conducted by reacting the nitro derivative (XXI) with a reducing agent such as sodium dithionate in water optionally in admixture with an alkanol, e.g. methanol, ethanol and the like.

The nitro derivative (XXI) in turn can be prepared from an intermediate (XXIII) by reaction with a suitable amine of formula (XXII).

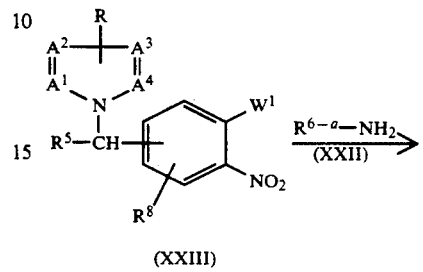

(XXIII)

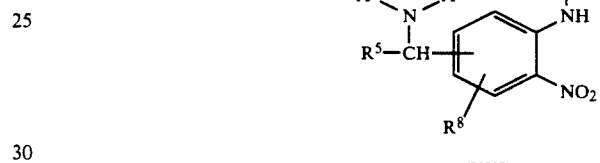

(XXI)

Said reaction can conveniently be conducted by stirring and, if desired, heating the reactants in a reaction-inert solvent such as, for example, an alkanol, e.g. methanol, ethanol, propanol, butanol, 1,2-ethanediol and the like, an ether, e.g. 1,1'-oxybisethane, tetrahydrofuran, 1,4-dioxane and the like, a dipolar aprotic solvent, e.g. N,N-dimethylformamide, dimethylsulfoxide, acetonitrile and the like, a halogenated solvent, e.g. trichloromethane, tetrachloromethane and the like; or a mixture of such solvents. The addition of a suitable base to pick up the acid which is liberated during the reaction may be appropriate; particularly convenient however is the use of an excess of the amine of formula (XXII).

The intermediates of formula (XXIII) can conveniently be prepared by nitration of a benzene derivative of formula (XXIV) following art-known nitration procedures.

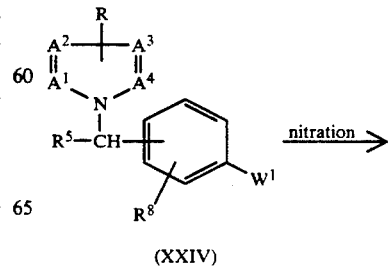

(XXIV)

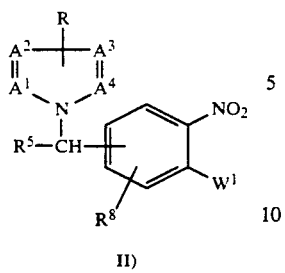

(II)

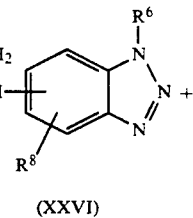

(XXVI)

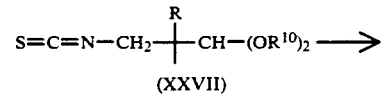

(XXVII)

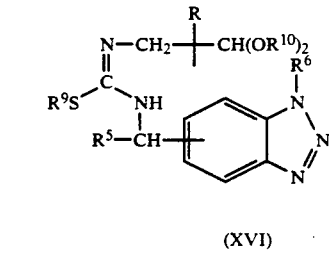

(XVI)

Said nitration reaction is conveniently conducted by treating the intermediate (XXIV) with nitric acid or the nitrate salt of (XXIV), in the presence concentrated sulfuric acid at low or ambient temperature. In some instances it may be appropriate to heat the reactants. Said nitration can be conducted without an additional solvent or may also be performed in a suitable solvent such as, for example, a halogenated hydrocarbon, e.g. trichloromethane, tetrachloromethane and the like, a carboxylic acid or a derivative thereof, e.g. acetic acid, acetic anhydride and the like solvents.

The intermediate hydrazines (XIX) or (XX) and amines may conveniently be prepared from a ketone of formula (X) or (XI) or by reaction with either an acid addition salt thereof, or with hydroxylamine or hydrazine or an acid addition salt or a solvate thereof, and reducing the thus obtained oxime or hydrazone, for example, by catalytic hydrogenation in the presence of hydrogen and an appropriate hydrogenation catalyst, e.g. Raney nickel and the like.

The intermediates of formula (XV) and (XVI) can be prepared from the corresponding amines of formula (XXV) and (XXVI) by reaction with a reagent of formula (XXVII) and optionally S-alkylating the thus obtained thiourea with a $C_{1-6}$alkylhalide.

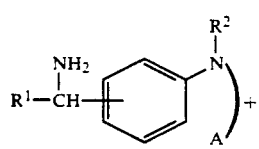

(XXV)

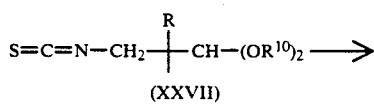

(XXVII)

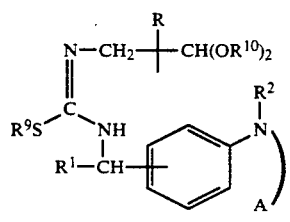

(XV)

From formulae (I) and (II) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

Pure stereochemically isomeric forms of the compounds of formulae (I) and (II) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure sterochemically isomeric forms of the appropriate starting materials, provided that the reaction occurs stereospecifically.

Stereochemically isomeric forms of the compounds of formulae (I) and (II) are naturally intended to be embraced within the scope of the invention.

An additional feature of the invention comprises the fact that those compounds of formula (I) wherein —$A^1$=$A^2$—$A^3$=$A^4$— is a bivalent radical of formula (y) or (z) or wherein —$A^1$=$A^2$—$A^3$=$A^4$— is a bivalent radical of formula (x) and R is $C_{1-6}$alkyl, the pharmaceutically acceptable acid addition salts thereof and the stereochemically isomeric forms thereof are novel compounds.

Particular novel compounds are those novel compounds wherein —$A^1$=$A^2$—$A^3$=$A^4$— is a bivalent radical of formula (y) or (z).

Preferred novel compounds within the invention are those particular novel compounds wherein —$A^1$=$A^2$—$A^3$=$A^4$— is a bivalent radical of formula (y); and/or $R^1$ is phenyl or halophenyl; and/or $R^2$ is hydrogen or $C_{1-4}$alkyl; and/or $R^3$ is hydrogen or $C_{1-4}$alkyl.

Some of the compounds of formula (I) and (II) which can be used as active ingredient in the compositions and methods of treatment according to the present invention are listed in the following tables with the purpose of illustrating the invention and not to limit it thereto.

TABLE 1

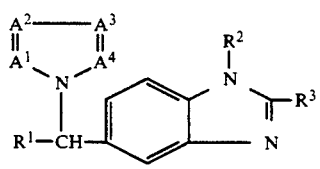

| Comp. No. | p* | $-A^1=A^2-A^3=A^4-$ | $R^1$ | $R^2$ | $R^3$ | mp.(°C.)/salt |
|---|---|---|---|---|---|---|
| 1 | 5 | —CH=CH—N=CH— | $C_6H_5$— | H— | $CH_3$— | 186.2 |
| 2 | 5 | —CH=CH—N=CH— | $C_6H_5$— | H— | $CH_3$— | 118.4 |
| 3 | 5 | —CH=CH—N=CH— | 2-thienyl- | H— | H— | 101.0 |
| 4 | 5 | —CH=CH—N=CH— | 2-thienyl- | H— | $CH_3$— | 108.9 |
| 5 | 5 | —CH=CH—N=CH— | 4-F—$C_6H_4$— | H— | $CH_3$— | 110.6 |
| 6 | 5 | —CH=CH—N=CH— | 2,4-$(Cl)_2$—$C_6H_3$— | H— | $CH_3$— | 138.4 |
| 7 | 5 | —CH=CH—N=CH— | 3-Cl—$C_6H_4$— | H— | $CH_3$— | 113.3 |
| 8 | 5 | —CH=CH—N=CH— | 3-$CH_3$—$C_6H_4$— | H— | H— | 104.8 |
| 9 | 5 | —CH=CH—N=CH— | $C_6H_5$— | H— | 2-pyridyl- | 123.3 |
| 10 | 5 | —CH=CH—N=CH— | c.$C_3H_5$— | H— | H— | 73.5 |
| 11 | 5 | —CH=CH—N=CH— | $C_6H_5$— | H— | 3-pyridiyl- | 133.1 |
| 12 | 6 | —N=CH—N=CH— | H— | OH— | 3-pyridiyl- | 219.3 |
| 13 | 5 | —CH=CH—N=CH— | $C_6H_5$— | H— | $C_6H_5$— | 134.5 |
| 14 | 6 | —N=CH—N=CH— | H—$OCH_3$— | | 3-pyridiyl- | 141.5 |
| 15 | 5 | —N=CH—N=CH— | H— | H— | $CH_3$— | 241.0/2HCl |
| 16 | 5 | —N=CH—N=CH— | H— | H— | H— | 184.4 |
| 17 | 5 | —N=CH—N=CH— | H— | H— | $C_6H_5$— | 239.7 |
| 18 | 5 | —N=CH—N=CH— | H— | H— | 3-pyridiyl- | 222.5 |
| 19 | 5 | —CH=CH—N=CH— | $C_6H_5$— | H— | $C_6H_5$—$CH_2$— | 189.9 |
| 20 | 5 | —CH=CH—N=CH— | $C_4H_9$— | H— | $CH_3$— | — |
| 21 | 5 | —CH=CH—N=CH— | $C_6H_5$— | $CH_3$— | H— | 138.7 |
| 22 | 5 | —CH=CH—N=CH— | i-$C_3H_7$— | H— | $CH_3$— | 214.8/2HCl/$H_2O$ |
| 23 | 5 | —CH=CH—N=CH— | $C_6H_5$— | H— | —CH=CH—(2-furyl) | 134.7(E) |
| 24 | 5 | —CH=CH—N=CH— | $C_3H_7$— | H— | $CH_3$— | 174.2/1.5$(COOH)_2$ |
| 25 | 5 | —CH=CH—N=CH— | $C_6H_5$— | H— | —CH=CH—(phenyl) | 140.6(E) |
| 26 | 5 | —CH=CH—N=CH— | 2-furanyl- | H— | H— | 150.9 |
| 27 | 5 | —CH=CH—N=CH— | $C_6H_5$— | H— | $CH_3$— | 77.2/$H_2O$/** |
| 28 | 5 | —CH=CH—N=CH— | 3-Cl—$C_6H_4$— | H— | H— | 200.2/HCl |
| 29 | 5 | —CH=CH—N=CH— | 3-Cl—$C_6H_4$— | $CH_3$— | H— | 131.2/1/2$H_2O$ |
| 30 | 5 | —CH=CH—N=CH— | 3-Cl—$C_6H_4$— | $C_6H_5$—$CH_2$— | H— | 59.6/1/2EtOH |
| 31 | 5 | —N=CH—N=CH— | 3-Cl—$C_6H_4$— | H— | $CH_3$— | 205.4/2$(COOH)_2$ |
| 32 | 5 | —N=CH—N=CH— | 3-Cl—$C_6H_4$— | H— | H— | 210.0 |
| 33 | 5 | —CH=CH—N=CH— | $C_6H_5$— | H— | $CH_3$— | 128.5/$H_2O$ |

*: p indicates the position of the 1H-azol-1-ylmethylmoiety on the benzimidazole ring
** = $[\alpha]_D$ = -29.7°(c = 0.5% in methanol)

TABLE 2

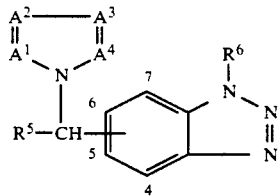

| Comp. No. | $-A^1=A^2-A^3=A^4-$ | p* | $R^5$ | $R^6$ | mp.(°C.)/salt |
|---|---|---|---|---|---|
| 34 | $-CH=CH-N=CH-$ | 5 | $C_6H_5-$ | $CH_3-$ | 111.9/HNO$_3$ |
| 35 | $-CH=CH-N=CH-$ | 5 | $C_6H_5-$ | $H-$ | 178.8 |
| 36 | $-CH=CH-N=CH-$ | 6 | $C_6H_5-$ | $CH_3-$ | 102.7 |
| 37 | $-N=CH-N=CH-$ | 5 | $C_6H_5-$ | $H-$ | 182.7 |
| 38 | $-CH=CH-N=CH-$ | 6 | $4-Cl-C_6H_4-$ | $CH_3-$ | 151.5/HCl/H$_2$O |
| 39 | $-N=CH-N=CH-$ | 6 | $4-Cl-C_6H_4-$ | $CH_3-$ | 178.9 |

*P indicates the position of the 1-H-azol-1-ylmethyl moiety on the benzotriazole ring.

The use of the compounds of formula (I) and (II), their pharmaceutically acceptable acid addition salts and their possible stereochemically isomeric forms in the method of the present invention is based on their useful property to delay the metabolism of retinoids, such as, all-trans-retinoic acid, 13-cis-retinoic acid and their derivatives. The latter results in more sustained-/higher tissue concentrations of retinoids and improved control of-differentiation and growth of various cell types. Said property to delay the metabolism of retinoids can easily be evidenced in various in vivo experiments. A particular test procedure is described hereinafter as the "Metabolism of endogenous or exogenously administered all-trans-retinoic acid"-test. As such, the compounds of formula (I) and (II) can be used to control the rate of growth and differentiation of normal, preneoplastic and neoplastic epithelial cells. The ability of retinoids, such as, 13-cis-retinoic acid, all-trans-retinoic acid and their derivatives to modulate differentiation and proliferation in several cell types is extensively studied and reviewed in J. Clin. Chem. Clin, Biochem., 26, 479-488 (1983); Pharmacological Reviews 36, 935-1005, (1984), Arch. Dermatol. 117, 160-180; (1981) and Journal of Medicinal Chemistry 25, 1269-1277, (1982).

The compounds of formulae (I) and (II), their pharmaceutically acceptable acid addition salts and their possible stereochemically isomeric forms are therefore useful in a method of treating disorders which are characterized by an increased proliferation and/or abnormal differentiation of epithelial cells. In particular the compounds of the invention can be used for treatment of carcinoma, which is essentially a derailment of cellular differentiation occurring in epithelial tissues. The compounds of the invention do not only exhibit an anticarcinogenic effect on estrogen or androgen dependent carcinoma cells but also show an unexpected effect on cells of which the growth and differentiation is not substantially mediated by or insensitive to the actions of androgens or estrogens, in particular on cells of which the growth and differentiation is sensitive to the actions of retinoids. Other uses include the ability to cure and-/or reduce a variety of disorders of keratinization such as, for example, acne, psoriasis, lamellar ichthyosis, plantar warts, callosities, acanthosis nigricans, lichen planus, molluscum, melasma, corneal epithelial abrasion, geographic tongue, Fox-Fordyce disease, cutaneous metastatic melanoma and keloids, epidermolytic hyperkeratosis, Darier's disease, pityriasis rubra pilaris, congenital ichthyosiform erythroderma, hyperkeratosis palmaris et plantaris, and similar disorders.

The anti-tumor activity, especially in retinoic acid sensitive tumors, may be demonstrated in several retinoic acid-sensitive cell lines and solid tumors such as, for example, in Ta3-Ha induced mamma tumors in female mice.

Those of skill in treating disorders which are characterized by an excessive proliferation and/or abnormal differentiation of tissues could determine the effective amount from the test results presented hereinafter. In general it is contemplated than an effective amount would be from 0.001 mg/kg to 50 mg/kg body weight and more preferably from 0.01 mg/kg to 10 mg/kg body weight.

The compounds of formulae (I) and (II) used the method of the invention are most preferably applied in the form of appropriate compositions. As appropriate compositions there may be cited all compositions usually employed for systemically or topically administering drugs. To prepare the pharmaceutical compositions of this invention, an effective amount of the particular compound, optionally in acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositons suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

As appropriate compositions for topical application there may be cited all compositions usually employed for topically administering drugs, e.g., creams, gellies, dressings, shampoos, tinctures, pastes, ointments, salves, powders, liquid or semiliquid formulation and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, pastes, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discreate units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

Other such compositions are preparations of the cosmetic type, such as toilet waters, packs, lotions, skin milks or milky lotions. Said preparations contain, besides the active ingredient of formula (I) or (II), components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrocloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient of formula (I) or (II) will be incorporated in said compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small ($<2\%$) amounts of preservative, colouring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts ($<2\%$) of preservative, dyestuff and/or perfume. In a skin milk, the carrier typically consists of 10–50% of oil, 1 to 10% of surfactant, 50–80% of water and 0 to 3% of preservative and/or perfume. In the aforementioned preparations, all % symbols refer to weight by weight percentage. The humectant, surfactant, oil, etc. . . . referred to in said preparations may be any such component used in the cosmetic arts but preferably will be one or more of the components mentioned hereinabove. Further, when in the above compositions one or more of the components make up the major part of the composition, the other ingredients can evidently be not present at their indicated maximum concentration and therefore will make up the remainder of the composition.

Particular compositions for use in the method of the present invention are those wherein the active ingredient of formula (I) or (II) is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

Water-soluble active ingredients such as, for example, most of the salt forms of the compound of formula (I) or (II) are encapsulated in the aqueous spaces between the molecular layers. The lipid soluble active ingredient of formula (I) or (II) is predominantly incorporated into the lipid layers, although polar head groups may protude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other art-known suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of the active ingredient of formula (I) or (II) is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated active ingredient of formula (I) or (II) can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatidylethanol-amine, phosphatydylserine, phosphatidylinositol, lysophosphatidylcholine and phosphatidyl glycerol, for example. Other lipophilic additives may be employed in order to selectively modify the characteristics of the liposomes. Examples of such other additives include stearylamine, phosphatidic acid, tocopherol, cholesterol and lanolin extracts.

It may be advantageous to use micronized forms of the active ingredient of formula (I) or (II), i.e., material having an average particle size of less than 10 microns, as the high surface area will facilitate the dissolution of the liposomal components.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

The liposome-formulated forms of the active ingredient of formula (I) or (II), particularly those obtained in the above-referred method of preparing such liposome formulated forms, may be used as such or in combination with any of the aforementioned carriers to prepare ointments, creams, gelées, toilet waters, etc. . . .

Apart from the above-described compositions, use may be made of covers, e.g. plasters, bandages, dressings, gauze pads and the like, containing an appropriate amount of a composition as referred hereinabove. In some cases use may be made of plasters, bandages, dressings, gauze pads and the like which have been impregnated or sprinkled with a liquid formulation containing the active agent, e.g. with an aseptic aqueous solution, or strewn with a powdery solid composition, or smeared, covered or coated with a semi-liquid composition.

In a further aspect of the invention there are provided particular pharmaceutical or cosmetical compositions which comprise an inert carrier, an effective amount of a compound of formula (I) and/or (II), an acid addition salt or a stereochemically isomeric form thereof and an effective amount of a retinoic acid, a derivative thereof or a stereochemically isomeric form thereof.

It can be demonstrated that the retinoic acids and the compounds of formula (I) and/or (II) act in a synergistic manner. Indeed, the combined effect of both substances is greater than the sum of their respective effects when administered separately. As evidenced by the data obtained in the "vaginal keratinization"-test described hereinafter. The above described retinoic acid containing compositions are particularly useful for treating acne or for retarding the effects of aging of the skin and generally improve the quality of the skin, particularly human facial skin. A pharmaceutical or cosmetical composition containing retinoic acid or a derivative thereof as the active ingredient in intimate admixture with a dermatologically acceptable carrier can be prepared according to conventional compounding techniques, such as those known for topical application of retinoic acid and its derivatives. Conventional pharmaceutical compounding techniques for topical application of retinoic acid are described for example in, U.S. Pat. Nos. 3,906,108 and 4,247,547, which are incorporated herein by reference. Preferred composition for topical application are in form of a cream, ointment or lotion comprising from 0.005 to 0.5% (particularly from 0.01 to 0.1%) all-trans-retinoic acid, 13-cis-retinoic acid or a derivative thereof and from 0.1 to 5% of a compound of formula (I) and/or (II), a dermatologically acceptable acid addition salt thereof or a stereochemically isomeric form thereof, in a semi-solid or liquid diluent or carrier.

These preferred composition should preferably be non-irritating and as far as possible they should be odorless and non-toxic. For convenience in applying to the skin, the composition usually contain, besides water or an organic solvent, several of certain organic emollients, emulsifiers for the aqueous and/or non aqueous phases of the compositions, wetting agents preservatives and agents that facilitate the penetration and remainence of the active agents in the skin.

In use, the retinoic acid containing compositions of the invention are applied topically to the area to be treated or protected, at regular intervals, as needed, generally about 7 to about 21 times per week. The duration of the treatment will depend upon the nature and severity of the condition to be treated as well as the frequency of application of the composition.

The following examples are intended to illustrate the scope of the present invention in all its aspects, and not to limit it thereto.

Experimental part

A. Preparation of the compounds

EXAMPLE 1

A mixture of 29.4 parts of 5-[chloro(3-chlorophenyl)-methyl]-2-methyl-1H-benzimidazole monohydrochloride, 18.6 parts of 1H-1,2,3-triazole and 240 parts of acetonitrile was stirred for 3 hours at reflux temperature. After evaporation to dry, the residue was taken up in water and treated with potassium carbonate. The product was extracted three times with 39 parts of dichloromethane. The combined extracts were dried, filtered and evaporated to dry. The residue was purified by column chromatography over silica gel using a mixture of dichloromethane and methanol (95:5 by volume) as eluent. The pure fractions were collected and the eluent was evaporated. The residue was converted into the ethanedioate salt in ethanol. The salt was filtered off and recrystallized from a mixture of ethanol and 2-propanone. The product was filtered off and dried, yielding 6.3 parts (14.0%) of 5-[(3-chlorophenyl)(1H-1,2,3-triazol-1-yl)methyl]-2-methyl-1H-benzimidazole ethanedioate(1:2); mp. 205.4° C. (comp.31).

EXAMPLE 2

A mixture of 5.6 parts of 1-methyl-α-phenyl-1H-benzimidazole-5-methanol, 4.05 parts of 1,1'-carbonyl-bis[1H-imidazole] and 54 parts tetrahydrofuran was stirred for 4 hours at reflux temperature. The tetrahydrofuran layer was evaporated and water was added to the residue. The decanted oil was dissolved in dichloromethane. The organic layer was dried, filtered and evaporated. The residue was purified by column chromatography over silica gel using a mixture of trichloromethane, methanol and methanol, saturated with ammonia, (90:5:5 by volume) as eluent. The pure fractions were collected and the eluent was evaporated. The residue was further purified by column chromatography over silica gel using a mixture of trichloromethane and methanol (93:7 by volume) as eluent. The pure fractions were collected and the eluent was evaporated. The residue was washed with 2,2'-oxybispropane and dried, yielding 2.9 parts (42.9%) of 5-[(1H-imidazol-1-yl)phenylmethyl]-1-methyl-1H-benzimidazole; mp. 138.7° C. (comp. 21).

EXAMPLE 3

A mixture of 6.2 parts of 4-[1-(1H-imidazol-1-yl)-2-methylpropyl]-1,2-benzenediamine, 6.5 parts of ethyl ethanimidate hydrochloride and 80 parts of ethanol was stirred for 3 hours at reflux temperature. After evaporation to dry, the residue was taken up in water and sodium carbonate. The product was extracted three times with 120 parts of trichloromethane. The combined extracts were dried, filtered and evaporated. The residue was purified by column chromatography over silica gel using a mixture of trichloromethane and methanol (95:5 by volume) as eluent. The pure fractions were collected and the eluent was evaporated. The residue was converted into the hydrochloride salt in a mixture of 2-propanone and ethanol. The salt was filtered off and crystallized from a mixture of ethanol and 2-propanone. The product was filtered off and dried, yielding 4 parts (44%) of 5-[1-(1H-imidazol-1yl)-2-methylpropyl]-2-methyl-1H-benzimidazole dihydrochloride.monohydrate; mp. 214.8° C. (comp. 22).

EXAMPLE 4

To a stirred and cooled (5° C.) solution of 5.2 parts of 4-[(1H-imidazol-1-yl)phenylmethyl]-1,2-benzenediamine in 4.8 parts of acetic acid and 20 parts of water was added a solution of 1.38 parts of sodium nitrite in 10 parts of water. The whole was stirred for 1 hour at room temperature. The reaction mixture was treated with a sodium hydrogen carbonate solution and the product was extracted with dichloromethane. The extract was dried, filtered and evaporated. The residue was crystallized from 64 parts of ethyl acetate. The product was filtered off and dried. yielding 4.7 parts (85.3%) of 5-[(1H-imidazol-1-yl)phenylmethyl]-1H-benzotriazole; mp. 178.8° C. (comp. 35).

All other compounds listed in Tables I and II can be obtained by analogous methods of preparation.

B. Pharmaceutical Examples

EXAMPLE 5

Metabolism of exogenously administered all-trans-retinoic acid

Male Wistar rats weighing 200~210 g were orally treated with vehicle (PEG 200) or with 40 mg/kg of a compound of formula (I). One hour later, the animals were anesthetized with ether and injected intrajugularly with 0.50 ml saline solution containing 20 μg of all-trans-retinoic acid. Two hours after this injection, rats were killed by decapitation and blood was collected on heparin. Blood samples were centrifuged (1000 g, 15 min) and plasma was recovered to determine the quantity of plasmatic all-trans-retinoic acid. The samples were analyzed by means of HPLC with UV-detection at 350 nm. Quantification was achieved by peak area integration and external standardization. Under the conditions used, plasma concentrations of the retinoic acid in vehiclepretreated animals were not detectable (<0.5 ng/ml), whereas compound nos. 1, 2, 3, 4, 5, 6, 7, 8, 9, 11, 13, 19, 20, 21, 22, 24, 28, 29, 30, 33 and 34 enhanced the recovery of all-trans-retinoic acid from the plasma to at least 8 ng/ml after dosing with 40 mg/kg.

EXAMPLE 6

Metabolism of endogenous all-trans-retinoic acid

Male Wistar rats weighing 200~210 g were orally treated with vehicle (PEG 200) or with 40 mg/kg of a compound of formula (I). Two hours after drug administration, the rats were killed by decapitation and blood was collected on heparin. Blood samples were centrifuged (1000 g, 15 min) and plasma was recovered to determine the quantity of plasmatic all-trans-retinoic acid. The samples were analyzed by means of HPLC with UV-detection at 350 nm. Quantification was achieved by peak area integration and external standardization. Under the conditions used, plasma concentrations of the retinoic acid in vehicle-pretreated animals were not detectable (<0.5 ng/ml), whereas compounds nos. 1, 2, 7, 13, 21, 22, 27, 28 and 33 enhanced the recovery of all-trans-retinoic acid from the plasma to at least 1 ng/ml.

EXAMPLE 7

Vaginal keratinization

Ovariectomized rats were injected subcutaneously with a sesame oil solution containing 100 μg of estradiol undecylate (Progynon Dépôt ®, Schering) in a volume of 0.1 ml per 100 g body weight. One and two days later, the animals were treated intravaginally with 200 μl of vehicle (PEG 200), all-trans-retinoic acid (1 or 4 μg) or all-trans-retinoic acid (1 μg) together with 3 mg of a compound of formula (I). One day after the second topical treatment, the animals were sacrificed. Vaginas were immediately dissected and trimmed of fat and connective tissue. The third middle of the organ (0.5 cm length) was fixed in liquid nitrogen for histological analysis. Hereto, a series of 10 μm cross-section were cut at −25° C., mounted onto gelatin-coated glass slides and stained with hematoxylin and eosin. The slides were examined under light microscopy at 100–400×magnification. The condition of the vaginal mucosa was scored (keratinization score) as 0: absence of keratinized squamae attached to the epithelial cells.

+: presence of keratinized squamae partially covering the epithelial cells.

++: presence of keratinized squamae covering the entire vaginal epithellium.

| Results | |
|---|---|
|  | score |
| vehicle (PEG 200) | ++ |
| 4 μg retinoic acid | 0 |
| 1 μg retinoic acid | ++ |
| 1 μg retinoic acid + 3 mg comp. No. 21 | 0 |

C. Composition Examples

The following formulations exemplify typical pharmaceutical and cosmetical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid addition salt or a sterochemically isomeric form thereof.

EXAMPLE 8

Oral Drops 500 g of the A.I. was dissolved in 0.5 l of 2-hydroxypropanoic acid and 1.5 l of the polyethylene glycol at 60°≈80° C. After cooling to 30°≈40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg of the A.I. (per ml). The resulting solution was filled into suitable containers.

EXAMPLE 9

ORAL SOLUTION 9 g of methyl 4-hydroxybenzoate and 1 part of propyl 4-hydroxy-benzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l 1,2,3-propane-triol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the A.I. per teaspoonful (5 ml). The resulting solution was filled in suitable containers.

EXAMPLE 10

CAPSULES 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 20 mg of the A.I.

EXAMPLE 11

FILM-COATED TABLETS

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10.000 tablets, each comprising 10 mg of the active ingredient.

Coating

To a solution of 10 g methyl cellulose (Methocel 60 HG ®) in 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propane-triol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated colour suspension (Opaspray K-1-2109®) and the whole was homogenated. The tablet cores were coated with the thus obtained mixture in a coating apparatus.

EXAMPLE 12

Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg A.I. per ml. The solution was sterilized by filtration (U.S.P. XVII p. 811) and filled in sterile containers.

EXAMPLE 13

Suppositories 3 g A.I. was dissolved in a solution of 3 g 2,3-dihydroxybutane-dioic acid in 25 ml polyethylene glycol 400. 12 g sorbitan ester surfactant (SPAN(®)) and hydrogenated cocoglyceride suppository base (Witepsol 555®) q.s. ad 300 g were molten together. The latter mixture was mixed well with the former solution. The thus obtained mixture was poured into moulds at a temperature of 37°-38° C. to form 100 suppositories each containing 30 mg of the active ingredient.

EXAMPLE 14

2% Cream 75 mg of stearyl alcohol, 2 mg of cetyl alcohol, 20 mg of sorbitan monostearate and 10 mg of isopropyl myristate are introduced into a doublewall jacketed vessel and heated until the mixture has completely molten. This mixture is added to a separately prepared mixture of purified water, 200 mg of propylene glycol and 15 mg of polysorbate 60 having a temperature of 70° to 75° C. while using a homogenizer for liquids. The resulting emulsion is allowed to cool to below 25° C. while continuously mixing. A solution of 20 mg of active ingredient of formula (I) or (II), 1 mg of polysorbate 80 and purified water and a solution of 2 mg of sodium sulfite anhydrous in purified water are next added to the emulsion while continuously mixing. The cream (1 g) is homogenized and filled into suitable tubes.

EXAMPLE 15

2% Topical Gel

To a solution of 200 mg of hydroxypropyl β-cyclodextrine in purified water is added 20 mg of active ingredient of formula (I) or (II) while stirring. Hydrochloric acid is added until complete solution and then sodium hydroxide is added until pH 6.0. This solution is added to a dispersion of 10 mg of carrageenan PJ in 50 mg of propylene glycol while mixing. While mixing slowly the mixture is heated to 50° C. and allowed to cool to about 35° C. whereupon 50 mg of ethyl alcohol 95% is added. The rest of the purified water is added q.s. ad 1 g and the mixture is mixed to homogenous.

EXAMPLE 16

2% Topical Cream

To a solution of 200 mg of hydroxypropyl β-cyclodextrine in purified water is added 20 mg of active ingredient of formula (I) or (II) while stirring. Hydrochloric acid is added until complete solution and next sodium hydroxide is added until pH 6.0. While stirring, 50 mg of glycerol and 35 mg of polysorbate 60 are added and the mixture is heated to 70° C. The resulting mixture is added to a mixture of 100 mg of mineral oil, 20 mg of stearyl alcohol, 20 mg of cetyl alcohol, 20 mg of glycerol monostearate and 15 mg of sorbate 60 having a temperature of 70° C. while mixing slowly. After cooling down to below 25° C., the rest of the purified water is added q.s. ad 1 g and the mixture is mixed to homogenous.

EXAMPLE 17

2% Liposome Formulation

A mixture of 2 g of active ingredient of formula (I) or (II) microfine, 20 g of phosphatidyl choline, 5 g of cholesterol and 10 g of ethyl alcohol is stirred and heated at 55°-60° C. until complete solution and is added to a solution of 0.2 g of methyl paraben, 0.02 g of propyl paraben, 0.15 g of disodium edetate and 0.3 g of sodium chloride in purified water while homogenizing. 1.5 g of hydroxypropylmethylcellulose in purified water is added ad 100 g and the mixing is continued until swelling is complete.

EXAMPLE 18

2% Liposome Formulation

A mixture of 10 g of phosphatidyl choline and 1 g of cholesterol in 7.5 g of ethyl alcohol is stirred and heated at 40° C. until complete solution. 2 g of active ingredient of formula (I) or (II) microfine is dissolved in purified water by mixing while heating at 40° C. The alcoholic solution is added slowly to the aqueous solution while homogenizing during 10 minutes. 1.5 g of hydroxypropylmethylcellulose in purified water is added while mixing until swelling is complete. The resulting solution is adjusted to pH 5.0 with sodium hydroxide 1N and diluted with the rest of the purified water ad 100 g.

We claim:

1. A method of treating subjects suffering from disorders which are characterized by an increased proliferation and/or abnormal differentiation of normal, preneoplastic or neoplastic epithelial cells by the systemic or topical administration to said subjects of an effective amount of a compound of formula

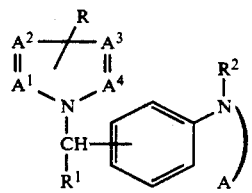

or

-continued

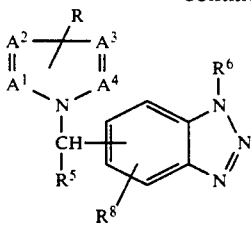
(II)

a pharmaceutically acceptable acid addition salt thereof or a stereochemically isomeric form thereof, wherein R, R$^1$, R$^2$, —A$^1$=A$^2$—A$^3$=A$^4$— and A in formula (I) have the following meaning —A$^1$=A$^2$—A$^3$=A$^4$— is a bivalent radical having the formula

  (x);

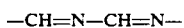  (y); or

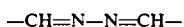  (z);

R is hydrogen or C$_{1-6}$alkyl;

R$^1$ is hydrogen; C$_{1-10}$alkyl; C$_{3-7}$cycloalkyl; Ar$^1$ or Ar$^1$—C$_{1-6}$alkyl;

R$^2$ is hydrogen; C$_{3-7}$cycloalkyl; Ar$^1$; C$_{1-10}$alkyl; C$_{1-6}$alkyl substituted with Ar$^1$ or C$_{3-7}$cycloalkyl; hydroxy; C$_{1-10}$alkyloxy; C$_{1-6}$alkyloxy substituted with Ar$^1$ or C$_{3-7}$cycloalkyl; C$_{3-6}$alkenyloxy optionally substituted with Ar$^2$; C$_{3-6}$alkynloxy optionally substituted with Ar$^2$; or Ar$^1$-oxy;

A is a bivalent radical having the formula

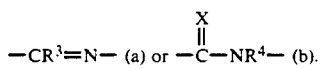

wherein the carbon atom in the bivalent radical (a) and (b) is connected to —NR$^2$;

said R$^3$ being hydrogen; halo; C$_{1-4}$alkyl substituted with up to 4 halo atoms; C$_{3-7}$cycloalkyl; Ar$^1$; quinolinyl; indolinyl; C$_{1-10}$alkyl; C$_{1-6}$alkyl substituted with Ar$^1$, C$_{3-7}$cycloalkyl, quinolinyl, indolinyl or hydroxy; C$_{1-10}$alkyloxy; C$_{1-6}$alkyloxy substituted with Ar$^1$ or C$_{3-7}$cycloalkyl; C$_{2-6}$alkenyl optionally substituted with Ar$^1$; Ar$^2$-oxy; C$_{1-6}$alkyloxycarbonyl; carboxyl; C$_{1-6}$alkylcarbonyl; Ar$^1$-carbonyl or Ar$^1$—(CHOH)—;

said X being O or S;

said R$^4$ being hydrogen, C$_{1-6}$alkyl or Ar$^2$—C$_{1-6}$alkyl;

wherein Ar$^1$ is phenyl, substituted phenyl, pyridinyl, aminopyridinyl, imidazolyl, thienyl, halothienyl, furanyl, halofuranyl or thiazolyl; and Ar$^2$ is phenyl or substituted phenyl; said substituted phenyl in Ar$^1$ and Ar$^2$ being phenyl substituted with 1, 2 or 3 substituents each independently selected from halo, hydroxy, trifluoromethyl, C$_{1-6}$alkyl, C$_{1-6}$alkyloxy, cyano, amino, mono- and di(C$_{1-6}$alkyl)amino, nitro, carboxyl, formyl and C$_{1-6}$alkyloxycarbonyl; and wherein R, R$^5$, R$^6$, R$^7$ and —A$^1$=A$^2$—A$^3$=A$^4$— in formula (II) have the following meaning —A$^1$=A$^2$—A$^3$=A$^4$— is a bivalent radical having the formula

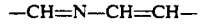  (x);

  (y); or

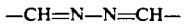  (z);

R is hydrogen or C$_{1-6}$alkyl;

R$^5$ is hydrogen; C$_{1-10}$alkyl; C$_{3-7}$cycloalkyl; Ar$^3$; Ar$^4$—C$_{1-6}$alkyl; C$_{2-6}$alkenyl or C$_{2-6}$alkynyl;

R$^6$ is hydrogen; C$_{1-10}$alkyl optionally substituted with Ar$^3$, C$_{3-7}$cycloalkyl, hydroxy or C$_{1-6}$alkyloxy; Ar$^3$; C$_{2-6}$alkenyl; C$_{2-6}$alkynyl; C$_{3-7}$cycloalkyl; bicyclo[2.2.1]heptan-2-yl; 2,3-dihydro-1H-indenyl; 1,2,3,4-tetrahydronaphthalenyl; or a radical of formula OR$^7$, R$^7$ is hydrogen; C$_{2-6}$alkenyl optionally substituted with Ar$^4$; C$_{2-6}$alkynyl; pyrimidinyl; di(Ar$^4$)methyl; 1-C$_{1-4}$alkyl-4-piperidinyl; or C$_{1-10}$alkyl optionally substituted with halo, hydroxy, C$_{1-6}$alkyloxy, amino, mono-and di(C$_{1-6}$alkyl)-amino, trifluoromethyl, carboxyl, C$_{1-6}$alkyloxycarbonyl, Ar$^3$, Ar$^4$—O—, Ar$^4$—S—, C$_{3-7}$cycloalkyl, 2,3-dihydro-1,4-benzodioxinyl, 1H-benzimidazolyl, C$_{1-4}$alkyl substituted 1H-benzimidazolyl, (1,1'-biphenyl)-4-yl or with 2,3-dihydro-2-oxo-1H-benzimidazolyl;

R$^8$ is hydrogen, nitro, amino, mono- and di(C$_{1-6}$alkyl)amino, halo, C$_{1-6}$alkyl, hydroxy or C$_{1-6}$alkyloxy;

wherein Ar$^3$ is phenyl, substituted phenyl, naphthalenyl, pyridinyl, aminopyridinyl, imidazolyl, triazolyl, thienyl, halothienyl, furanyl, C$_{1-6}$alkylfuranyl, halofuranyl or thiazolyl; Ar$^4$ is phenyl, substituted phenyl or pyridinyl, said substituted phenyl in Ar$^3$ and Ar$^4$ being phenyl substituted with up to 3 substituents each independently selected from halo, hydroxy, hydroxymethyl, trifluoromethyl, C$_{1-6}$alkyl, C$_{1-6}$alkyloxy, C$_{1-6}$alkyloxycarbonyl, carboxyl, formyl, (hydroxyimino)methyl, cyano, amino, mono-and di(C$_{1-6}$alkyl)amino and nitro.

2. A method according to claim 1 wherein the compound is a compound of formula (I) wherein the 1H-azol-1-ylmethyl moiety is substituted on either the 5 or 6 position of the benzimidazole ring; R is hydrogen; R$^1$ is hydrogen; C$_{1-6}$alkyl; C$_{3-7}$cycloalkyl; phenyl; substituted phenyl; thienyl or furanyl optionally substituted with halo; R$^2$ is hydrogen; C$_{3-7}$cycloalkyl; phenyl; substituted phenyl; pyridinyl; C$_{1-6}$alkyl optionally monosubstituted with phenyl, C$_{3-7}$cycloalkyl, pyridinyl or thienyl; hydroxyl, C$_{1-6}$alkyloxy optionally monosubstituted with phenyl, pyridinyl, thienyl or C$_{3-6}$cycloalkyl; C$_{3-6}$alkenyloxy optionally monosubstituted with phenyl; or C$_{3-6}$alkynyloxy; R$^3$ is hydrogen; C$_{1-4}$alkyl substituted with up to 4 halo atoms; C$_{3-7}$cycloalkyl; phenyl; substituted phenyl; imidazolyl; thiazolyl; thienyl; furanyl; quinolinyl; pyridinyl optionally substituted with amino, C$_{1-10}$alkyl; C$_{1-5}$alkyl optionally monosubstituted with phenyl, pyridinyl, imidazolyl, thienyl, indolyl or hydroxyl; C$_{1-4}$alkyloxy optionally monosubstituted with phenyl; C$_{2-6}$alkenyl optionally monosubstituted with pyridinyl, furanyl, imidazolyl or phenyl; carboxyl; C$_{1-4}$alkyloxycarbonyl; phenylcarbonyl; or hydroxy and phenylmethyl; and R$^4$ is hydrogen or phenylC$_{1-4}$alkyl.

3. A method according to claim 1 wherein the compound is a compound of formula II wherein the 1H-azol-1-ylmethyl moiety is substituted on either the 5 or 6 position of the benzotriazole ring; R is hydrogen; R$^5$ is hydrogen; C$_{1-6}$alkyl; phenyl; substituted phenyl; C$_{3-7}$cycloalkyl; thienyl or furanyl optionally substituted with halo; R$^6$ is hydrogen; C$_{1-6}$alkyl; C$_{3-6}$alkenyl; C$_{3-6}$alkynyl; C$_{3-7}$cycloalkyl; phenyl; substituted phenyl; bicylo[2.2.1]heptan-2-yl; 2,3-dihydro-1H-indenyl;

1,2,3,4-tetrahydronaphthalenyl; $C_{1-6}$alkyl monosubstituted with phenyl, substituted phenyl, naphthalenyl, thienyl, furanyl, $C_{1-4}$alkylfuranyl, $C_{3-7}$cycloalkyl, hydroxy, $C_{1-4}$alkyloxy; or $R^6$ is a radical $-OR^7$ with $R^7$ being hydrogen, $C_{1-6}$alkyl, $C_{3-6}$alkenyl, phenylC$_{3-6}$alkenyl, $C_{3-6}$alkynyl, pyrimidinyl, diphenylmethyl, (1-$C_{1-4}$ alkyl-4-piperidinyl), $C_{1-6}$alkyl substituted with halo, hydroxy, amino, mono- or di($C_{1-6}$alkyl)amino, trifluoromethyl, carboxyl, $C_{1-6}$alkyloxycarbonyl, phenyl, substituted phenyl, thienyl, furanyl, $C_{1-4}$alkylfuranyl, pyridinyl, phenoxy, phenylthio, 2,3-dihydro-1,4-benzodioxinyl, 1H-benzimidazolyl, $C_{1-4}$alkyl substituted 1Hbenzimidazolyl, (1,1'-biphenyl)-4-yl or 2,3-dihydro-2-oxo-1H-benzimidazolyl; and $R^8$ is hydrogen.

4. A method according to claim 2 wherein $R^1$ is hydrogen, $C_{1-6}$alkyl, phenyl, substituted phenyl, thienyl or furanyl; $R^2$ is hydrogen, $C_{1-6}$alkyl, or $C_{1-4}$alkyl substituted with phenyl; $R^3$ is hydrogen, $C_{1-6}$alkyl, phenyl, pyridinyl, $C_{1-6}$alkyl, $C_{1-6}$alkyl monosubstituted with phenyl or $C_{2-6}$alkenyl optionally monosubstituted with furanyl or phenyl; and $R^4$ is hydrogen.

5. A method according to claim 3 wherein $R^5$ is hydrogen, $C_{1-6}$alkyl, phenyl, substituted phenyl, thienyl or furanyl; $R^6$ is hydrogen, $C_{1-6}$alkyl, $C_{1-6}$alkyl substituted with phenyl, or a radical of formula $-OR^7$ with $R^7$ being hydrogen or $C_{1-6}$alkyl.

6. A method according to claim 4 wherein $R^1$ is $C_{1-4}$alkyl, phenyl, phenyl substituted with one or two halo, $C_{1-4}$alkyl or $C_{1-4}$alkyloxy substituents, or thienyl; and $R^2$ is hydrogen or $C_{1-4}$alkyl; and $R^3$ is hydrogen or $C_{1-4}$alkyl.

7. A method according to claim 5 wherein $R^5$ is $C_{1-4}$alkyl, phenyl or phenyl substituted with one or two halo, $C_{1-4}$alkyl or $C_{1-4}$alkyloxy substituents; and $R^6$ is hydrogen or $C_{1-4}$alkyl.

8. A method according to claim 6 wherein $R^1$ is phenyl or halophenyl, and $R^2$ and $R^3$ are both independently hydrogen or $C_{1-4}$alkyl.

9. A method according to claim 7 wherein $R^5$ is phenyl or halophenyl, and $R^6$ is hydrogen or $C_{1-4}$alkyl.

10. A method according to claim 1 whereby said normal, preneoplastic and neoplastic epithelial cells are cells of which the growth and differentiation is not substantially mediated by the actions of androgens and estrogens.

11. A method according to claim 1 whereby said normal, preneoplastic and neoplastic epithelial cells are cells of which the growth and differentiation is sensitive to the actions of retinoids.

12. A method for retarding the effects of aging of the skin which comprises applying topically to the surface of the skin an effective amount of a compound according to claim 1.

13. A method for controlling the rate of growth and differentiation of normal, preneoplastic and neoplastic epithelial cells by the systemic or topical administration of an effective amount of a compound of the formula:

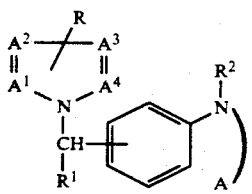

(I)

or

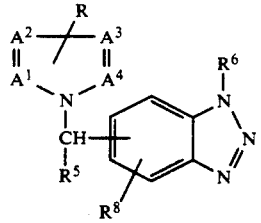

(II)

a pharmaceutically acceptable acid addition salt thereof or a stereochemically isomeric form thereof, wherein:
R, $R^1$, $R^2$, $-A^1=A^2-A^3=A^4-$, and A in formula (I) have the following meanings:
$-A^1=A^2-A^3=A^4-$ represents a bivalent radical having the formula:

$-CH=N-CH=CH-$      (x);

$-CH=N-CH=N-$      (y); or $-CH=N-N=CH-$      (z);

R represents hydrogen or $C_{1-6}$alkyl;
$R^1$ represents hydrogen; $C_{1-10}$alkyl; $C_{3-7}$cycloalkyl; $Ar^1$; or $Ar^1-C_{1-6}$alkyl;
$R^2$ represents hydrogen; $C_{3-7}$cycloalkyl; $Ar^1$; $C_{1-10}$alkyl, $C_{1-6}$alkyl substituted with $Ar^1$ or $C_{3-7}$cycloalkyl; hydroxy; $C_{1-10}$alkyloxy; $C_{1-6}$alkyloxy substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$—oxy; and
A represents a bivalent radical having the formula $-CR^3=N-$      (a) or $-(C=X)-NR^4-$      (b)

wherein the carbon atom in the bivalent radical (a) and (b) is connected to $-NR^2$; and wherein:
$R^3$ represents hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, $C_{3-7}$cycloalkyl, quinolinyl, indolinyl, or hydroxy; $C_{1-10}$alkyloxy; $C_{1-6}$alkyloxy substituted with $Ar^1$ or $C_{3-7}$cycloalkyl; $C_{2-6}$alkenyl optionally substituted with $Ar^1$; $Ar^2$-oxy; $C_{1-6}$alkyloxycarbonyl; carboxyl; $C_{1-6}$alkylcarbonyl; $Ar^1$-carbonyl; or $Ar^1-(CHOH)-$;
X represents O or S; and
$R^4$ represents hydrogen, $C_{1-6}$alkyl or $Ar^2-C_{1-6}$alkyl;
wherein in the foregoing $Ar^1$ represents phenyl, substituted phenyl, pyridinyl, aminopyridinyl, imidazolyl, thienyl, halothienyl, furanyl, halofuranyl or thiazolyl; and $Ar^2$ represents phenyl or substituted phenyl; said substituted phenyl in $Ar^1$ and $Ar^2$ being phenyl substituted with 1, 2, or 3 substituents each independently selected from halo, hydroxy, trifluoromethyl, $C_{1-6}$alkyl, cyano, amino, mono- and di($C_{1-6}$alkyl)amino, nitro, carboxyl, formyl, and $C_{1-6}$alkyloxycarbonyl;
and wherein R, $R^5$, $R^6$, $R^7$, and $-A^1=A^2-A^3=A^4-$ in formula (II) have the following meanings:
$-A^1=A^2-A^3=A^4-$ represents a bivalent radical of the formula:

$-CH=N-CH=CH-$      (x);

—CH=N—CH=N— (y); or

—CH=N—N=CH— (z);

R represents hydrogen or $C_{1-6}$alkyl;

$R^5$ represents hydrogen; $C_{1-10}$alkyl; $C_{3-7}$cycloalkyl; $Ar^3$; $Ar^4$—$C_{1-6}$alkyl; $C_{2-6}$alkyl; $C_{2-6}$alkenyl or $C_{2-6}$alkynyl;

$R^6$ represents hydrogen; $C_{1-10}$alkyl optionally substituted with $Ar^3$, $C_{2-6}$alkenyl; $C_{3-7}$cycloalkyl, hydroxy or $C_{1-6}$alkyloxy; $Ar^3$; $C_{2-6}$alkynyl; $C_{3-7}$cycloalkyl; bicyclo[2.2.1]heptan-2-yl; 2,3-dihydro-1H-indenyl; 1,2,3,4-tetrahydronaphthalenyl; or a radical of formula $OR^7$, $R^7$ represents hydrogen; $C_{2-6}$alkenyl optionally substituted with $Ar^4$; $C_{2-6}$alkynyl; pyrimidinyl, di($Ar^4$)methyl; 1-$C_{1-4}$alkyl-4-piperidinyl; or $C_{1-10}$alkyl optionally substituted with halo, hydroxy, $C_{1-6}$alkyloxy, amino, mono- and di($C_{1-6}$alkyl)amino, trifluoromethyl, carboxyl, $C_{1-6}$alkyloxycarbonyl, $Ar^3$, $Ar^4$—O—, $Ar^4$—S—, $C_{3-7}$cycloalkyl, 2,3-dihydro-1,4benzodioxinyl, 1H-benzimidazolyl, $C_{1-4}$alkyl substituted 1H-benzimidazolyl, (1,1'-biphenyl)-4-yl or with 2,3-dihydro-2-oxo-1H-benzimidazolyl; and $R^8$ represents hydrogen, nitro, amino, mono- and di($C_{1-6}$alkyl)amino, halo, $C_{1-6}$alkyl, hydroxy or $C_{1-6}$alkyloxy;

wherein in the foregoing $Ar^3$ represents phenyl, substituted phenyl, naphthalenyl, pyridinyl, aminopyridinyl, imidazolyl, triazolyl, thienyl, halothienyl, furanyl, $C_{1-6}$alkylfuranyl, halofuranyl or thiazolyl; $Ar^4$ represents phenyl, substituted phenyl or pyridinyl, said substituted phenyl in $Ar^3$ and $Ar^4$ being phenyl substituted with up to 3 substituents each independently selected from halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro.

14. A method of reducing or curing acne in subjects suffering from acne, said method comprising the topical administration to said subjects of an amount effective in reducing or curing acne of a compound of the formula:

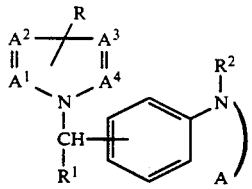

(I)

or

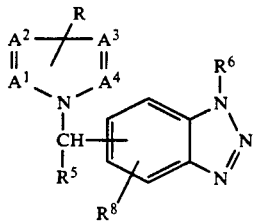

(II)

a pharmaceutically acceptable acid addition salt thereof or a stereochemically isomeric form thereof, wherein:

R, $R^1$, $R^2$, —$A^1$=$A^2$—$A^3$=$A^4$—, and A in formula (I) have the following meanings:

—$A^1$=$A^2$—$A^3$=$A^4$— represents a bivalent radical having the formula:

—CH=N—CH=CH— (x);

—CH=N—CH=N— (y); or

—CH=N—N=CH— (z);

R represents hydrogen or $C_{1-6}$alkyl;

$R^1$ represents hydrogen; $C_{1-10}$alkyl; $C_{3-7}$cycloalkyl; $Ar^1$; or $Ar^1$—$C_{1-6}$alkyl;

$R^2$ represents hydrogen; $C_{3-7}$cycloalkyl; $Ar^1$; $C_{1-10}$alkyl, $C_{1-6}$alkyl substituted with $Ar^1$ or $C_{3-7}$cycloalkyl; hydroxy; $C_{1-10}$alkyloxy; $C_{1-6}$alkyloxy substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$-oxy; and A represents a bivalent radical having the formula —$CR^3$=N— (a) or —(C=X)—$NR^4$— (b)

wherein the carbon atom in the bivalent radical (a) and (b) is connected to —$NR^2$; and wherein:

$R^3$ represents hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, $C_{3-7}$cycloalkyl, quinolinyl, indolinyl, or hydroxy; $C_{1-10}$alkyloxy; $C_{1-6}$alkyloxy substituted with $Ar^1$ or $C_{3-7}$cycloalkyl; $C_{2-6}$alkenyl optionally substituted with $Ar^1$; $Ar^2$-oxy; $C_{1-6}$alkyloxycarbonyl; carboxyl; $C_{1-6}$alkylcarbonyl; $Ar^1$-carbonyl; or $Ar^1$—(CHOH)—;

X represents O or S; and $R^4$ represents hydrogen, $C_{1-6}$alkyl or $Ar^2$—$C_{1-6}$alkyl;

wherein in the foregoing $Ar^1$ represents phenyl, substituted phenyl, pyridinyl, aminopyridinyl, imidazolyl, thienyl, halothienyl, furanyl, halofuranyl or thiazolyl; and $Ar^2$ represents phenyl or substituted phenyl; said substituted phenyl in $Ar^1$ and $Ar^2$ being phenyl substituted with 1, 2, or 3 substituents each independently selected from halo, hydroxy, trifluoromethyl, $C_{1-6}$alkyl, cyano, amino, mono- and di($C_{1-6}$alkyl)amino, nitro, carboxyl, formyl, and $C_{1-6}$alkyloxycarbonyl;

and wherein R, $R^5$, $R^6$, $R^7$, and —$A^1$=$A^2$—$A^3$=$A^4$— in formula (II) have the following meanings:

—$A^1$=$A^2$—$A^3$=$A^4$— represents a bivalent radical of the formula:

—CH=N—CH=CH— (x);

—CH=N—CH=N— (y); or

—CH=N—N=CH— (z);

R represents hydrogen or $C_{1-6}$alkyl;

$R^5$ represents hydrogen; $C_{1-10}$alkyl; $C_{3-7}$cycloalkyl; $Ar^3$; $Ar^4$—$C_{1-6}$alkyl; $C_{2-6}$alkyl; $C_{2-6}$alkenyl or $C_{2-6}$alkynyl;

$R^6$ represents hydrogen; $C_{1-10}$alkyl optionally substituted with $Ar^3$, $C_{2-6}$alkenyl; $C_{3-7}$cycloalkyl, hydroxy or $C_{1-6}$alkyloxy; $Ar^3$; $C_{2-6}$alkynyl; $C_{3-7}$cycloalkyl; bicyclo [2.2.1]heptan-2-yl; 2,3- dihydro-1H-indenyl; 1,2,3,4-tetrahydronaphthalenyl; or a radical of formula OR$^7$, R$^7$ represents hydrogen; C$_{2-6}$alkenyl optionally substituted with Ar$^4$; C$_{2-6}$alkynyl; pyrimidinyl, di(Ar$^4$)methyl; 1-C$_{1-4}$alkyl-4-piperidinyl; or C$_{1-10}$alkyl optionally substituted with halo, hydroxy, C$_{1-6}$alkyloxy, amino, mono- and di(C$_{1-6}$alkyl)amino, trifluoromethyl, carboxyl, C$_{1-6}$alkyloxycarbonyl, Ar$^3$, Ar$^4$—O—, Ar$^4$—S—, C$_{3-7}$cycloalkyl, 2,3-dihydro-1,4-benzodioxinyl, 1H-benzimidazolyl, C$_{1-4}$alkyl substituted 1H-benzimidazolyl, (1,1'-biphenyl)-4-yl or with 2,3-dihydro-2-oxo-1H-benzimidazolyl; and R$^8$ represents hydrogen, nitro, amino, mono- and di(C$_{1-6}$alkyl)amino, halo, C$_{1-6}$alkyl, hydroxy or C$_{1-6}$alkyloxy;

wherein in the foregoing Ar$^3$ represents phenyl, substituted phenyl, naphthalenyl, pyridinyl, aminopyridinyl, imidazolyl, triazolyl, thienyl, halothienyl, furanyl, C$_{1-6}$alkylfuranyl, halofuranyl or thiazolyl; Ar$^4$ represents phenyl, substituted phenyl or pyridinyl, said substituted phenyl in Ar$^3$ and Ar$^4$ being phenyl substituted with up to 3 substituents each independently selected from halo, hydroxy, hydroxymethyl, trifluoromethyl, C$_{1-6}$alkyl, C$_{1-6}$alkyloxy, C$_{1-6}$alkyloxycarbonyl, carboxyl, formyl, (hydroxyimino)methyl, cyano, amino, mono- and di(C$_{1-6}$alkyl)amino and nitro.

15. A method of inhibiting the metabolism of retinoic acid in mammals by the systemic or topical administration to said mammals of an amount effective in inhibiting the degradation of retinoic acid of a compound of the formula:

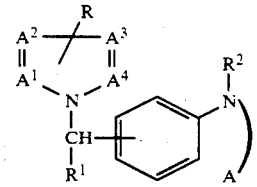

(I)

or

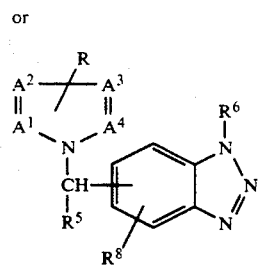

(II)

a pharmaceutically acceptable acid addition salt thereof or a stereochemically isomeric form thereof, wherein:
R, R$^1$, R$^2$, —A$^1$=A$^2$—A$^3$=A$^4$—, and A in formula (I) have the following meanings:
—A$^1$=A$^2$—A$^3$=A$^4$— represents a bivalent radical having the formula:

—CH=N—CH=CH— (x);

—CH=N—CH=N— (y); or

—CH=N—N=CH— (z);

R represents hydrogen or C$_{1-6}$alkyl;

R$^1$ represents hydrogen; C$_{1-10}$alkyl; C$_{3-7}$cycloalkyl; Ar$^1$; or Ar$^1$—C$_{1-6}$alkyl;

R$^2$ represents hydrogen; C$_{3-7}$cycloalkyl; Ar$^1$; C$_{1-10}$alkyl, C$_{1-6}$alkyl substituted with Ar$^1$ or C$_{3-7}$cycloalkyl; hydroxy; C$_{1-10}$alkyloxy; C$_{1-6}$alkyloxy substituted with Ar$^1$ or C$_{3-7}$cycloalkyl; C$_{3-6}$alkenyloxy optionally substituted with Ar$^2$; C$_{3-6}$alkynyloxy optionally substituted with Ar$^2$; or Ar$^1$-oxy; and A represents a bivalent radical having the formula —CR$^3$=N— (a) or —(C=X)—NR$^4$— (b)

wherein the carbon atom in the bivalent radical (a) and (b) is connected to —NR$^2$; and wherein:

R$^3$ represents hydrogen; halo; C$_{1-4}$alkyl substituted with up to 4 halo atoms; C$_{3-7}$cycloalkyl; Ar$^1$; quinolinyl; indolinyl; C$_{1-10}$alkyl; C$_{1-6}$alkyl substituted with Ar$^1$, C$_{3-7}$cycloalkyl, quinolinyl, indolinyl, or hydroxy; C$_{1-10}$alkyloxy; C$_{1-6}$alkyloxy substituted with Ar$^1$ or C$_{3-7}$cycloalkyl; C$_{2-6}$alkenyl optionally substituted with Ar$^1$; Ar$^2$-oxy; C$_{1-6}$alkyloxycarbonyl; carboxyl; C$_{1-6}$alkylcarbonyl; Ar$^1$-carbonyl; or Ar$^1$—(CHOH)—;

X represents O or S; and

R$^4$ represents hydrogen, C$_{1-6}$alkyl or Ar$^2$—C$_{1-6}$alkyl;

wherein in the foregoing Ar$^1$ represents phenyl, substituted phenyl, pyridinyl, aminopyridinyl, imidazolyl, thienyl, halothienyl, furanyl, halofuranyl or thiazolyl; and Ar$^2$ represents phenyl or substituted phenyl; said substituted phenyl in Ar$^1$ and Ar$^2$ being phenyl substituted with 1, 2, or 3 substituents each independently selected from halo, hydroxy, trifluoromethyl, C$_{1-6}$alkyl, cyano, amino, mono- and di(C$_{1-6}$alkyl)amino, nitro, carboxyl, formyl, and C$_{1-6}$alkyloxycarbonyl;

and wherein R, R$^5$, R$^6$, R$^7$, and —A$^1$=A$^2$—A$^3$=A$^4$— in formula (II) have the following meanings:
—A$^1$=A$^2$—A$^3$=A$^4$— represents a bivalent radical of the formula:

—CH=N—CH=CH— (x);

—CH=N—CH=N— (y); or

—CH=N—N=CH— (z);

R represents hydrogen or C$_{1-6}$alkyl;

R$^5$ represents hydrogen; C$_{1-10}$alkyl; C$_{3-7}$cycloalkyl; Ar$^3$; Ar$^4$—C$_{1-6}$alkyl; C$_{2-6}$alkyl; C$_{2-6}$alkenyl or C$_{2-6}$alkynyl;

R$^6$ represents hydrogen; C$_{1-10}$alkyl optionally substituted with Ar$^3$, C$_{2-6}$alkenyl; C$_{3-7}$cycloalkyl, hydroxy or C$_{1-6}$alkyloxy; Ar$^3$; C$_{2-6}$alkynyl; C$_{3-7}$cycloalkyl; bicyclo heptan-2-yl; 2,3-dihydro-1H-indenyl; 1,2,3,4-tetrahydronaphthalenyl; or a radical of formula OR$^7$, R$^7$ represents hydrogen; C$_{2-6}$alkenyl optionally substituted with Ar$^4$; C$_{2-6}$alkynyl; pyrimidinyl, di(Ar$^4$)methyl; 1-C$_{1-4}$alkyl-4-piperidinyl; or C$_{1-10}$alkyl optionally substituted with halo, hydroxy, C$_{1-6}$alkyloxy, amino, mono- and di(C$_{1-6}$alkyl)amino, trifluoromethyl, carboxyl, C$_{1-6}$alkyloxycarbonyl, Ar$^3$, Ar$^4$—O—, Ar$^4$—S—, C$_{3-7}$cycloalkyl, 2,3-dihydro-1,4-benzodioxinyl, 1H-benzimidazolyl, C$_{1-4}$alkyl substituted 1H- benzimidazolyl, (1,1'-biphenyl)-4-yl or with 2,3-dihydro-2-oxo-1H-benzimidazolyl; and $R^8$ represents hydrogen, nitro, amino, mono- and di($C_{1-6}$alkyl)amino, halo, $C_{1-6}$alkyl, hydroxy or $C_{1-6}$alkyloxy;

wherein in the foregoing $Ar^3$ represents phenyl, substituted phenyl, naphthalenyl, pyridinyl, aminopyridinyl, imidazolyl, triazolyl, thienyl, halothienyl, furanyl, $C_{1-6}$alkylfuranyl, halofuranyl or thiazolyl; $Ar^4$ represents phenyl, substituted phenyl or pyridinyl, said substituted phenyl in $Ar^3$ and $Ar^4$ being phenyl substituted with up to 3 substituents each independently selected from halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro.

16. A method for treating subjects suffering from psoriasis comprising the topical administration to said subjects of an effective antipsoriatic amount of a compound of the formula:

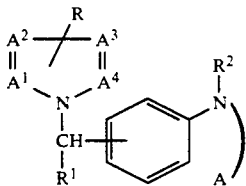
(I)

or

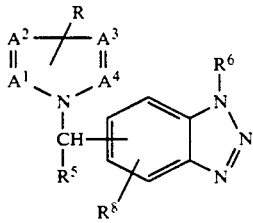
(II)

a pharmaceutically acceptable acid addition salt thereof or a stereochemically isomeric form thereof, wherein: R, $R^1$, $R^2$, $-A^1=A^2-A^3=A^4-$, and A in formula (I) have the following meanings:

$-A^1=A^2-A^3=A^4-$ represents a bivalent radical having the formula:

$-CH=N-CH=CH-$ (x);

$-CH=N-CH=N-$ (y); or $-CH=N-N=CH-$ (z);

R represents hydrogen or $C_{1-6}$alkyl;

$R^1$ represents hydrogen; $C_{1-10}$alkyl; $C_{3-7}$cycloalkyl; $Ar^1$; or $Ar^1-C_{1-6}$alkyl;

$R^2$ represents hydrogen; $C_{3-7}$cycloalkyl; $Ar^1$; $C_{1-10}$alkyl, $C_{1-6}$alkyl substituted with $Ar^1$ or $C_{3-7}$cycloalkyl; hydroxy; $C_{1-10}$alkyloxy; $C_{1-6}$alkyloxy substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$-oxy; and A represents a bivalent radical having the formula $-CR^3=N-$ (a) or $-(C=X)-NR^4-$ (b)

wherein the carbon atom in the bivalent radical (a) and (b) is connected to $-NR^2$; and wherein:

$R^3$ represents hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, $C_{3-7}$cycloalkyl, quinolinyl, indolinyl, or hydroxy; $C_{1-10}$alkyloxy; $C_{1-6}$alkyloxy substituted with $Ar^1$ or $C_{3-7}$cycloalkyl; $C_{2-6}$alkenyl optionally substituted with $Ar^1$; $Ar^2$-oxy; $C_{1-6}$alkyloxycarbonyl; carboxyl; $C_{1-6}$alkylcarbonyl; $Ar^1$-carbonyl; or $Ar^1-(CHOH)-$;

X represents O or S; and $R^4$ represents hydrogen, $C_{1-6}$alkyl or $Ar^2-C_{1-6}$alkyl;

wherein in the foregoing $Ar^1$ represents phenyl, substituted phenyl, pyridinyl, aminopyridinyl, imidazolyl, thienyl, halothienyl, furanyl, halofuranyl or thiazolyl; and $Ar^2$ represents phenyl or substituted phenyl; said substituted phenyl in $Ar^1$ and $Ar^2$ being phenyl substituted with 1, 2, or 3 substituents each independently selected from halo, hydroxy, trifluoromethyl, $C_{1-6}$alkyl, cyano, amino, mono- and di($C_{1-6}$alkyl)amino, nitro, carboxyl, formyl, and $C_{1-6}$alkyloxycarbonyl;

and wherein R, $R^5$, $R^6$, $R^7$, and $-A^1=A^2-A^3=A^4-$ in formula (II) have the following meanings:

$-A^1=A^2-A^3=A^4-$ represents a bivalent radical of the formula:

$-CH=N-CH=CH-$ (x);

$-CH=N-CH=N-$ (y); or $-CH=N-N=CH-$ (z);

R represents hydrogen or $C_{1-6}$alkyl;

$R^5$ represents hydrogen; $C_{1-10}$alkyl; $C_{3-7}$cycloalkyl; $Ar^3$; $Ar^4-C_{1-6}$alkyl; $C_{2-6}$alkyl; $C_{2-6}$alkenyl or $C_{2-6}$alkynyl;

$R^6$ represents hydrogen; $C_{1-10}$alkyl optionally substituted with $Ar^3$, $C_{2-6}$alkenyl; $C_{3-7}$cycloalkyl, hydroxy or $C_{1-6}$alkyloxy; $Ar^3$; $C_{2-6}$alkynyl; $C_{3-7}$cycloalkyl; bicyclo[2.2.1]heptan-2-yl; 2,3-dihydro-1H-indenyl; 1,2,3,4-tetrahydronaphthalenyl; or a radical of formula $OR^7$, $R^7$ represents hydrogen; $C_{2-6}$alkenyl optionally substituted with $Ar^4$; $C_{2-6}$alkynyl; pyrimidinyl, di($Ar^4$)methyl; 1-$C_{1-4}$alkyl-4-piperidinyl; or $C_{1-10}$alkyl optionally substituted with halo, hydroxy, $C_{1-6}$alkyloxy, amino, mono- and di($C_{1-6}$alkyl)amino, trifluoromethyl, carboxyl, $C_{1-6}$alkyloxycarbonyl, $Ar^3$, $Ar^4-O-$, $Ar^4-S-$, $C_{3-7}$cycloalkyl, 2,3-dihydro-1,4-benzodioxinyl, 1H-benzimidazolyl, $C_{1-4}$alkyl substituted 1H-benzimidazolyl, (1,1'-biphenyl)-4-yl or with 2,3-dihydro-2-oxo-1H-benzimidazolyl; and $R^8$ represents hydrogen, nitro, amino, mono- and di($C_{1-6}$alkyl)amino, halo, $C_{1-6}$alkyl, hydroxy or $C_{1-6}$alkyloxy;

wherein in the foregoing $Ar^3$ represents phenyl, substituted phenyl, naphthalenyl, pyridinyl, aminopyridinyl, imidazolyl, triazolyl, thienyl, halothienyl, furanyl, $C_{1-6}$alkylfuranyl, halofuranyl or thiazolyl; $Ar^4$ represents phenyl, substituted phenyl or pyridinyl, said substituted phenyl in $Ar^3$ and $Ar^4$ being phenyl substituted with up to 3 substituents each independently selected from halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro.

17. The method according to claim 15 wherein the compound is 5-[(3-chlorophenyl) (1H-imidazole-1-yl)methyl]-1H-benzimidazole or an acid addition salt thereof.

18. The method according to claim 17 wherein the acid addition salt is the monohydrochloride salt.

* * * * *

UNITED STATES PATENT AND TRADEMARK OFFICE
CERTIFICATE OF CORRECTION

PATENT NO. : 5,157,046
DATED : October 20, 1992
INVENTOR(S) : Jean P. F. Van Wauwek et al It is certified that error appears in the above-indentified patent and that said Letters Patent is hereby corrected as shown below:

In column 34, claim 1, lines 60-65, Formula (I) should appear as follows (valence line from "A" to the benzene ring was omitted):

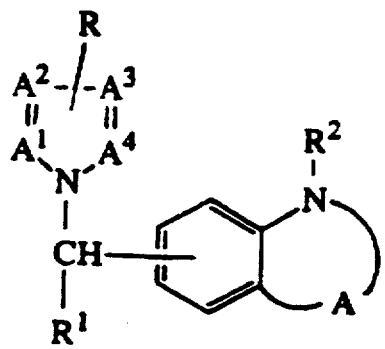

In columns 37, 39, 41 and 43, (claims 13, 14, 15 and 16) lines 60-65, 49-55, 36-44 and 25-30, Formula (I) should appear as follows (valence line from "A" to the benzene ring was omitted):

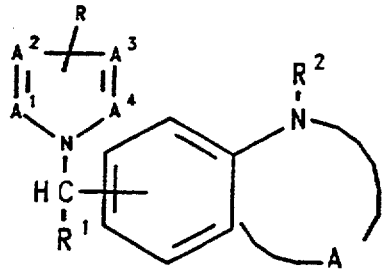

UNITED STATES PATENT AND TRADEMARK OFFICE
CERTIFICATE OF CORRECTION

PATENT NO. : 5,157,046
DATED : October 20, 1992
INVENTOR(S) : Jean P. F. Van Wauwek, et al It is certified that error appears in the above-indentified patent and that said Letters Patent is hereby corrected as shown below:

In column 35, line 30, delete "$C_{3-6}$alkynloxy" and insert therefor --$C_{3-6}$alkynyloxy--.

In column 42, line 57, "bicyclo heptan-2-yl" should read --bicyclo[2.2.1]heptan-2-yl--.

Signed and Sealed this

Tenth Day of January, 1995

Attest:

BRUCE LEHMAN

Attesting Officer

Commissioner of Patents and Trademarks